United States Patent
Doyle

(10) Patent No.: US 9,205,017 B2
(45) Date of Patent: Dec. 8, 2015

(54) ADAPTIVE ARM SUPPORT SYSTEMS AND METHODS FOR USE

(75) Inventor: Mark C. Doyle, Del Mar, CA (US)

(73) Assignee: LEVITATE TECHNOLOGIES, INC., San Diego, CA (US)

( * ) Notice: Subject to any disclaimer, the term of this patent is extended or adjusted under 35 U.S.C. 154(b) by 728 days.

(21) Appl. No.: 13/353,268

(22) Filed: Jan. 18, 2012

(65) Prior Publication Data
US 2012/0184880 A1    Jul. 19, 2012

Related U.S. Application Data

(60) Provisional application No. 61/433,840, filed on Jan. 18, 2011, provisional application No. 61/507,535, filed on Jul. 13, 2011.

(51) Int. Cl.
*A61F 2/78*    (2006.01)
*A61F 5/01*    (2006.01)
(Continued)

(52) U.S. Cl.
CPC ............ *A61H 1/0281* (2013.01); *A61F 5/0118* (2013.01); *B25J 9/0006* (2013.01); *A61F 2/78* (2013.01); *A61F 2002/7862* (2013.01); *A61F 2005/0134* (2013.01);
(Continued)

(58) Field of Classification Search
CPC ........... A41D 13/08; B25J 11/00; A61H 1/00; A61F 5/0102; A61F 5/0118; A61F 5/3738; A61F 2005/0134; A61F 2005/0197; A61F 2/54; A61F 2/546
USPC ................. 623/57–61, 65; 601/5, 33; 602/36; 224/189, 201, 628, 663; 297/411.35; 248/118; 108/50.14
See application file for complete search history.

(56) References Cited

U.S. PATENT DOCUMENTS 4,180,870 A * 1/1980 Radulovic et al. .............. 623/26
4,298,149 A * 11/1981 Gottschalk et al. ........... 224/201
(Continued)

FOREIGN PATENT DOCUMENTS

GB    2472036 B    12/2013
JP    10071161 A    3/1998
(Continued)

OTHER PUBLICATIONS

Derwent abstract of WO2009040908A1. Y Sankai. Published Apr. 2, 2009.*
(Continued)

*Primary Examiner* — Thomas J Sweet
*Assistant Examiner* — Christie Bahena
(74) *Attorney, Agent, or Firm* — William A. English; Vista IP Law Group LLP

(57) ABSTRACT

A system is provided for supporting an arm of a user that includes a harness configured to be worn by the user, and an arm support coupled to the harness and including an arm rest to support an arm of the user. The arm support is configured to accommodate and follow movement of the arm without substantially interfering in such movement. The arm support may at least partially offset a gravitational force acting on the arm as the user moves and the arm support follows the movement of the user's arm. For example, the arm support may transfer at least a portion of the weight of the user's arm to the torso or other region of the user's body and/or may apply an opposing force to at least partially offset the gravitational force acting on the arm.

14 Claims, 46 Drawing Sheets

(51) Int. Cl.
    *A61H 1/02*     (2006.01)
    *B25J 9/00*     (2006.01)

(52) U.S. Cl.
    CPC   *A61F 2005/0155* (2013.01); *A61F 2005/0179* (2013.01); *A61H 2201/0165* (2013.01); *A61H 2201/1215* (2013.01); *A61H 2201/1238* (2013.01); *A61H 2201/165* (2013.01); *A61H 2201/1616* (2013.01); *A61H 2201/1671* (2013.01); *A61H 2201/5007* (2013.01); *A61H 2201/5064* (2013.01); *A61H 2230/625* (2013.01)

(56) References Cited

U.S. PATENT DOCUMENTS

| | | | |
|---|---|---|---|
| 5,111,983 A | | 5/1992 | Simmons et al. |
| 5,873,847 A * | | 2/1999 | Bennett et al. .................. 602/16 |
| 6,301,526 B1 * | | 10/2001 | Kim et al. ..................... 700/260 |
| 8,641,782 B2 * | | 2/2014 | Kim et al. ........................ 623/58 |
| 2003/0120183 A1 * | | 6/2003 | Simmons ..................... 600/595 |
| 2010/0217163 A1 * | | 8/2010 | Sankai ............................. 601/5 |
| 2011/0127390 A1 | | 6/2011 | Brown |

FOREIGN PATENT DOCUMENTS

| | | | |
|---|---|---|---|
| JP | 2002153115 A | 5/2002 |
| JP | 2009273711 A | 5/2008 |
| JP | 2008295696 A | 12/2008 |
| WO | WO 2009029693 A1 | 3/2009 |
| WO | WO 2012099995 A3 | 7/2012 |
| WO | WO 2013106532 A1 | 7/2013 |
| WO | WO 2013155065 A1 | 10/2013 |

OTHER PUBLICATIONS

Rahman, Tariq. Passive exoskeletons for assisting limb movement. Journal of Rehabilitation and Development. vol. 43. No. 5. Sep. 2006. pp. 583-590.*

Written Opinion of the International Searching Authority dated Aug. 31, 2012 in International Application No. PCT/US2012/02177 filed Jan. 18, 2012, Form ISA 237, (4 pages).

PCT International Search Report dated Nov. 11, 2013 in International Application No. PCT/US2013/052782 filed Jul. 30, 2013, Form ISA 210, (3 pages).

* cited by examiner

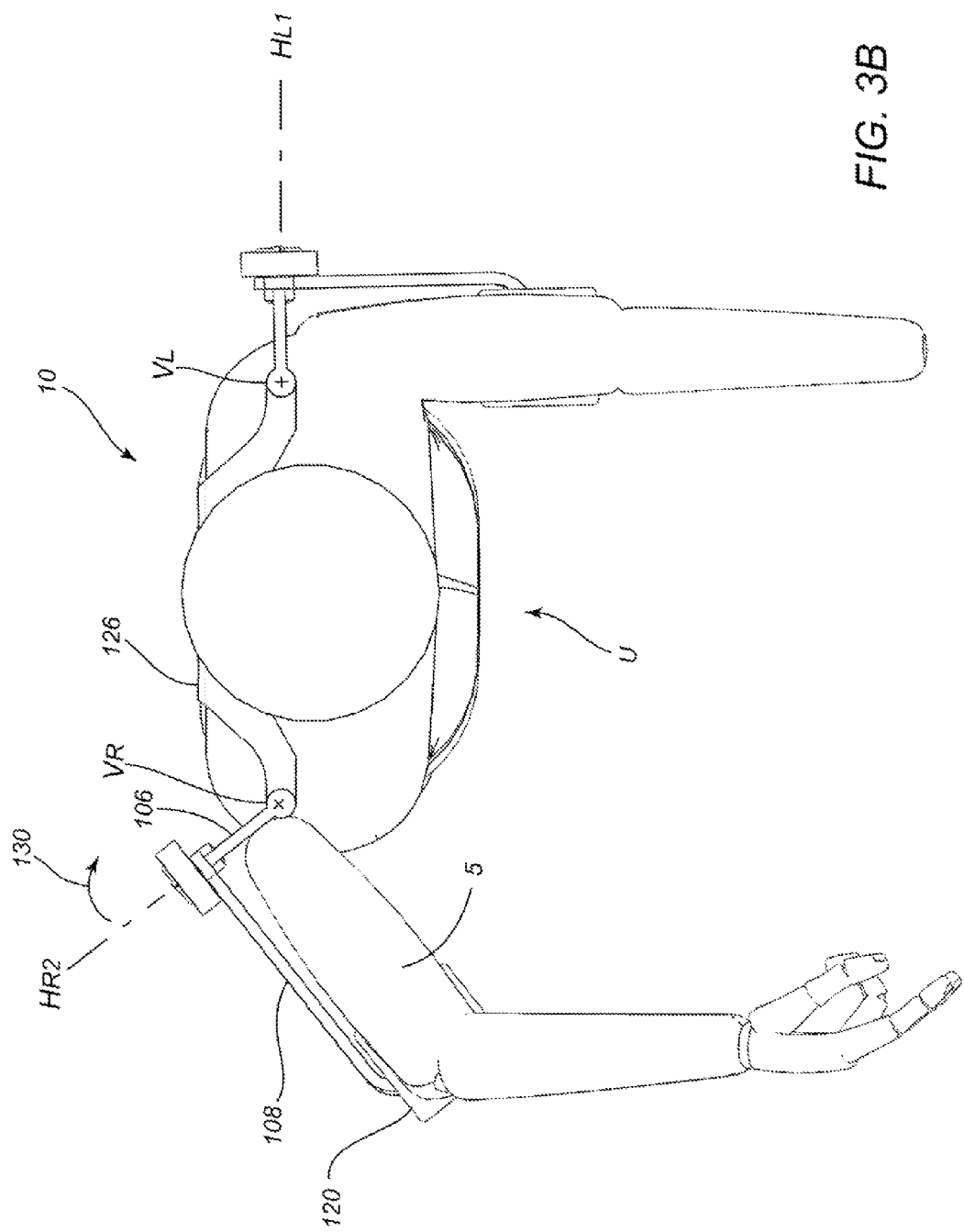

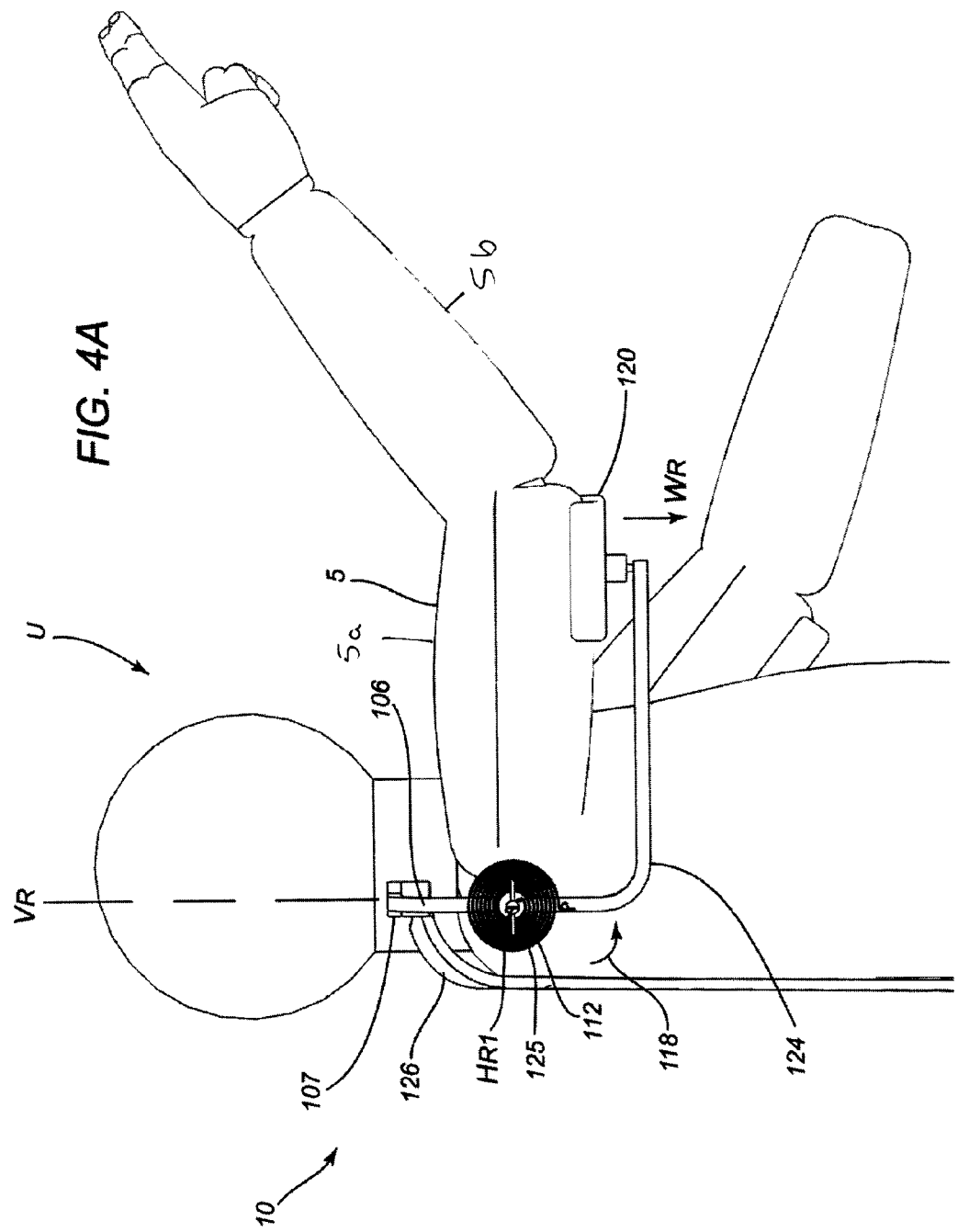

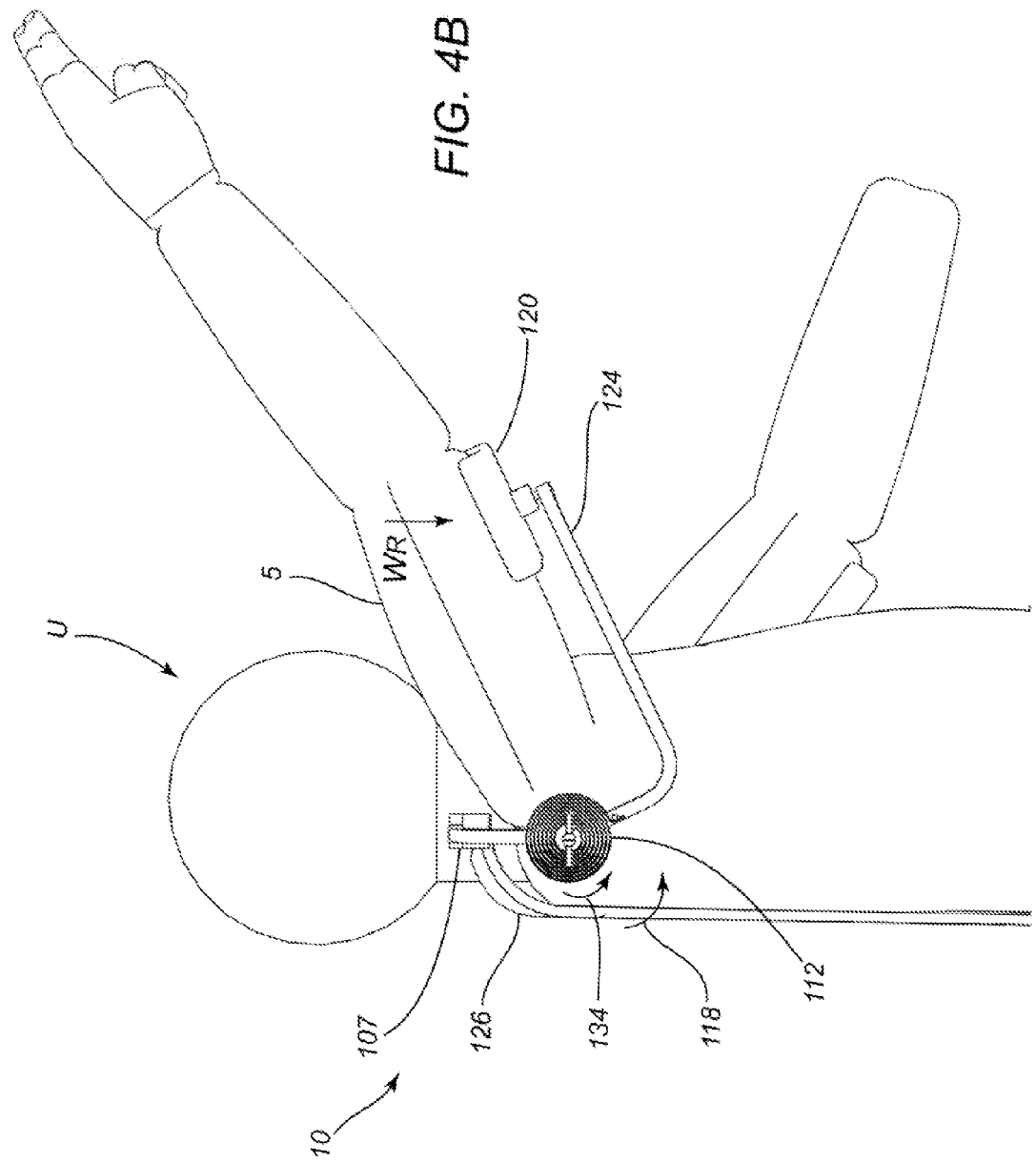

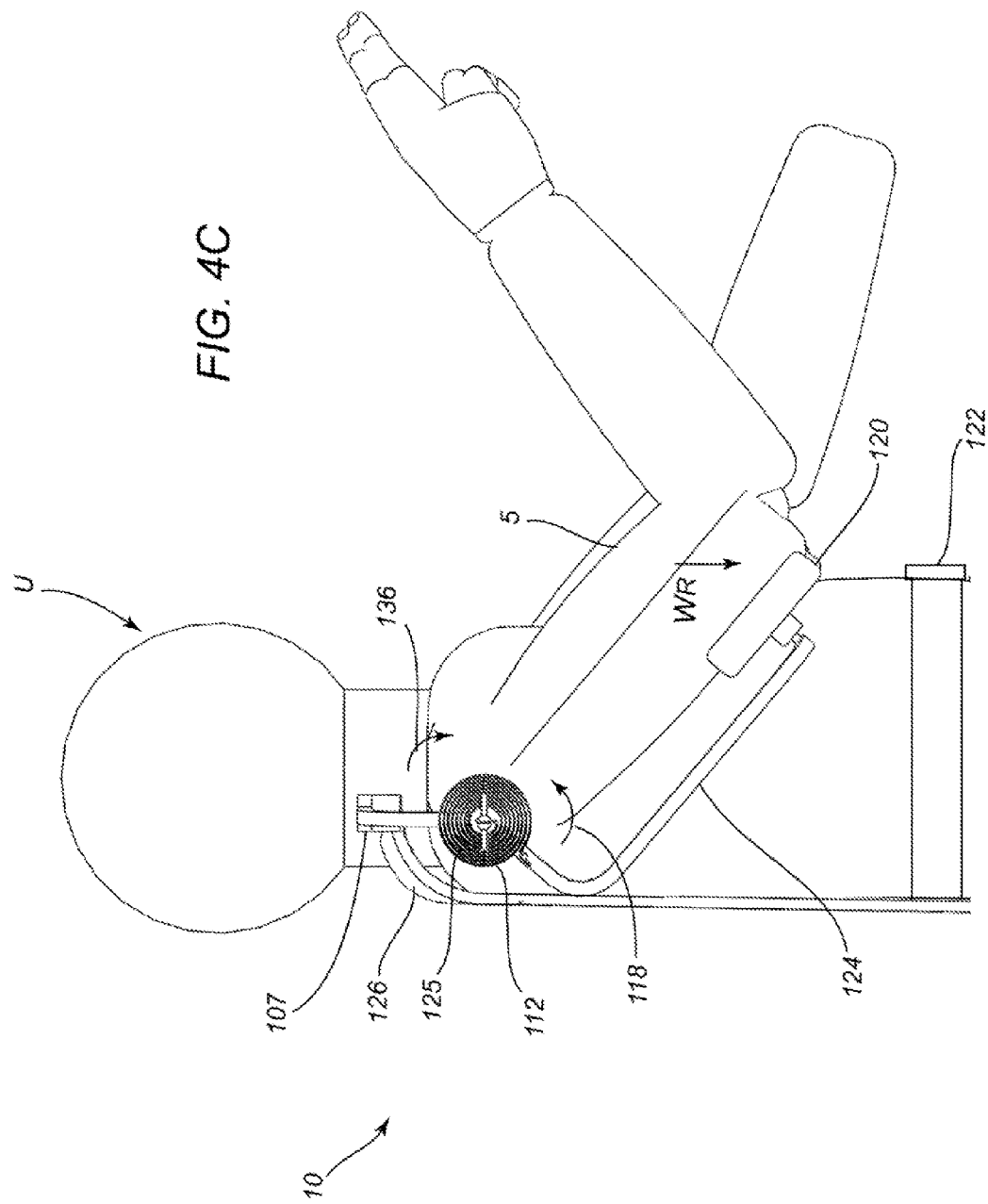

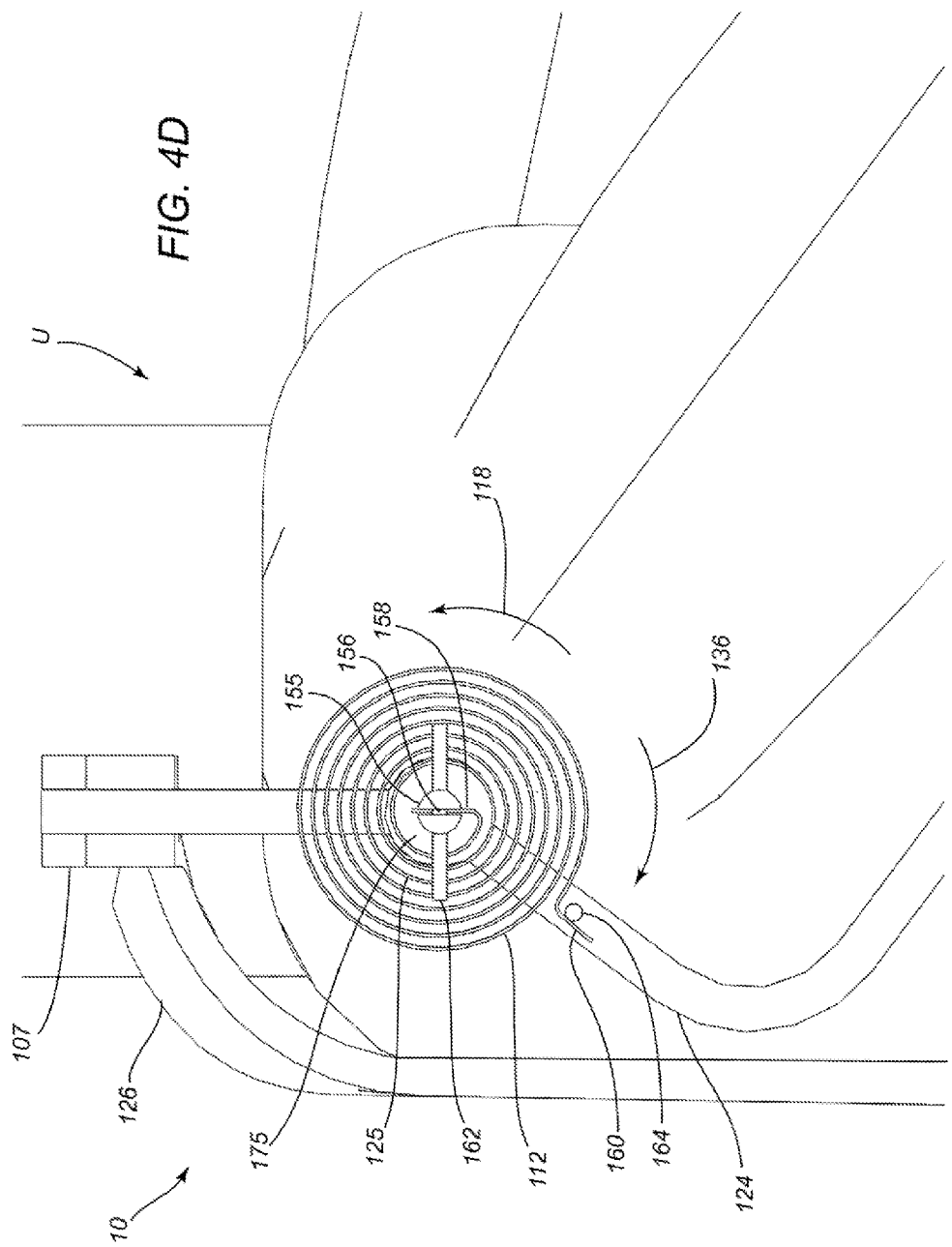

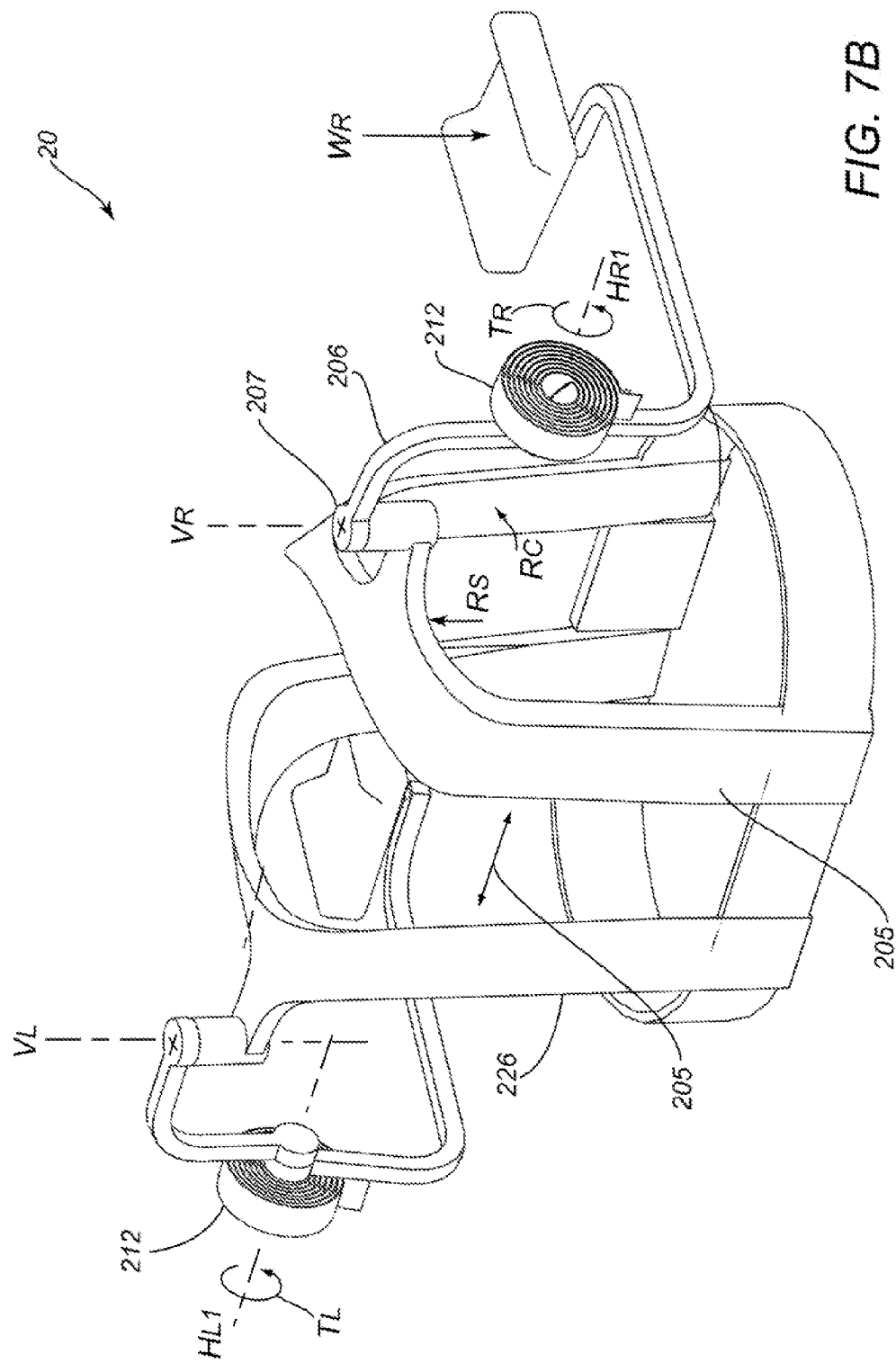

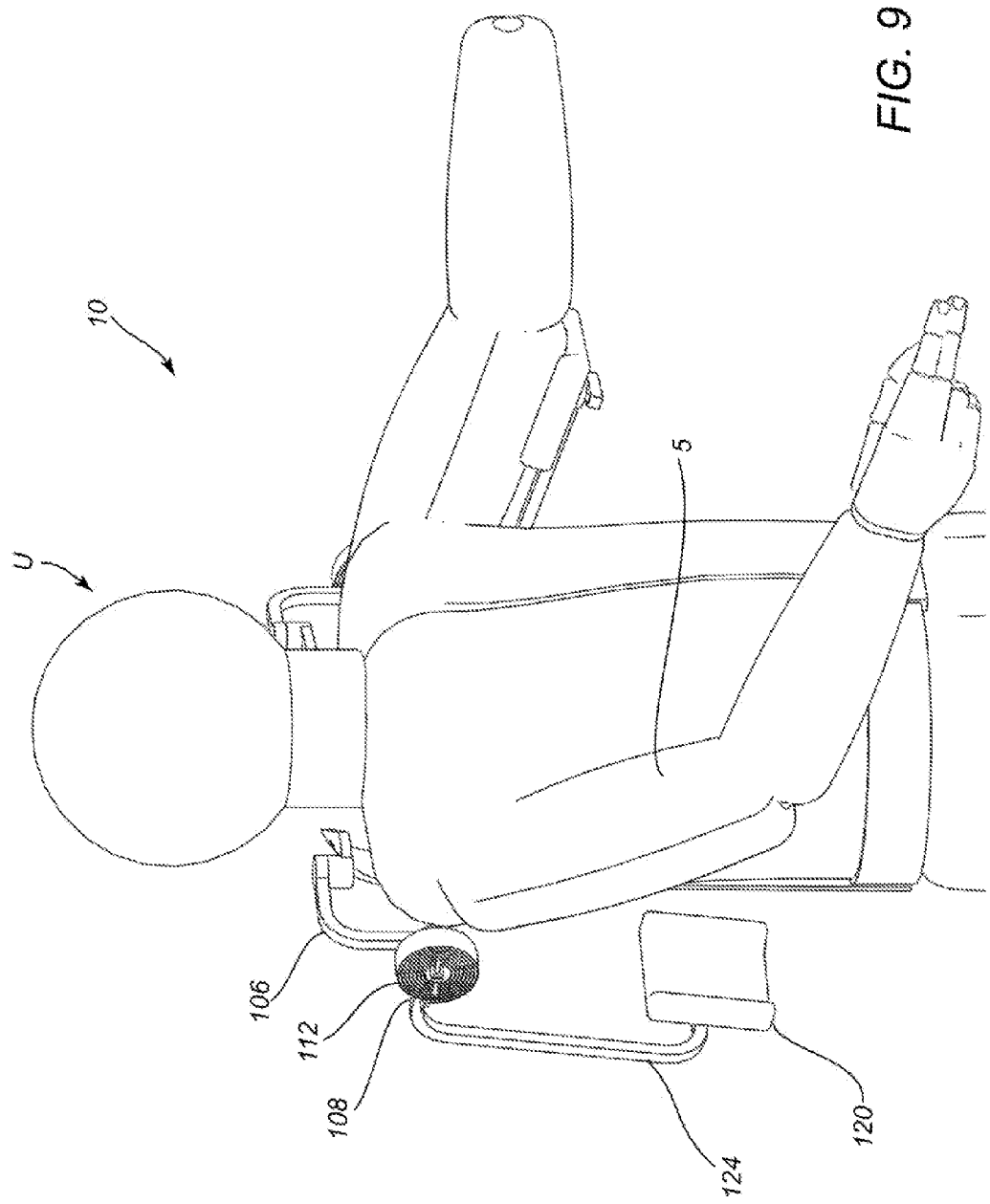

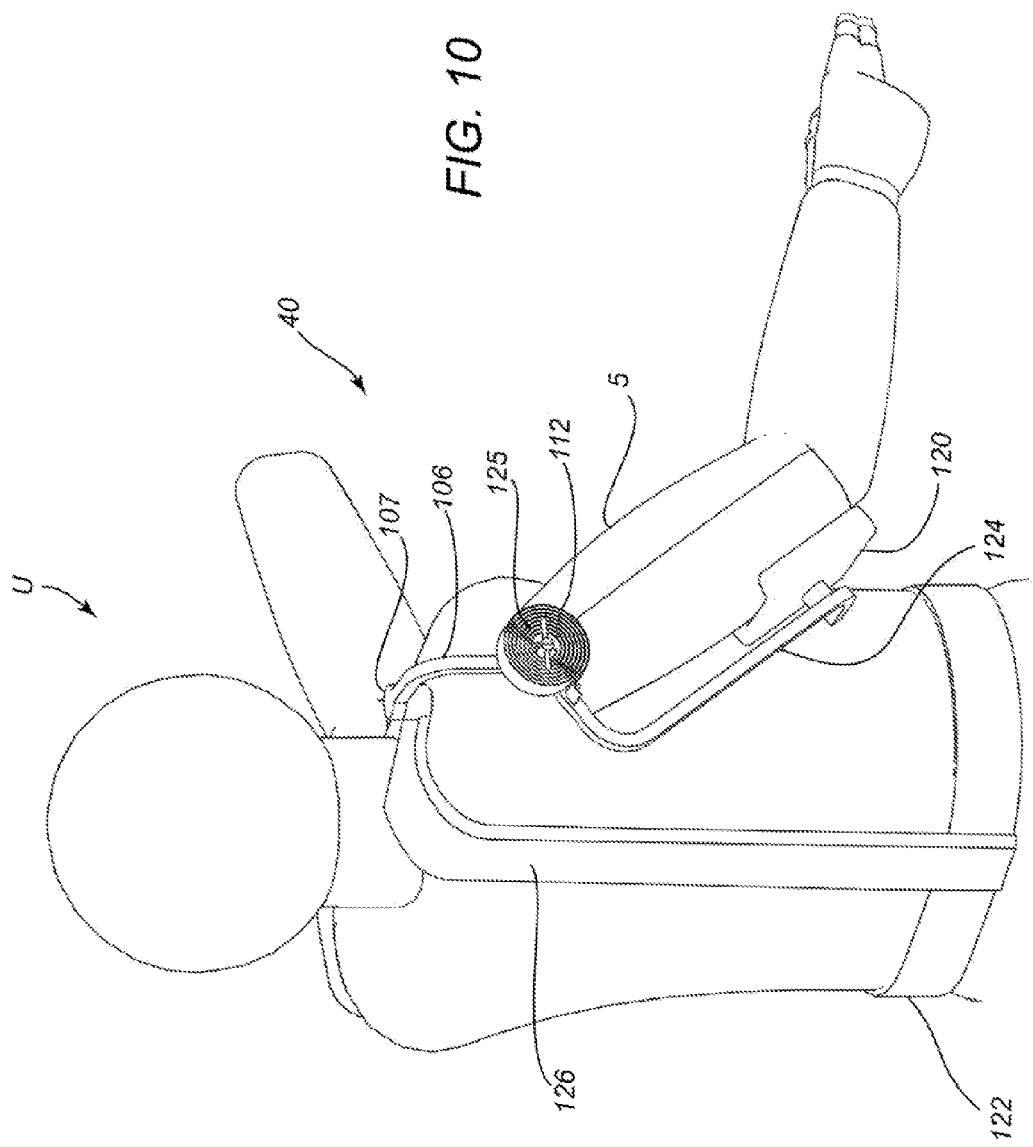

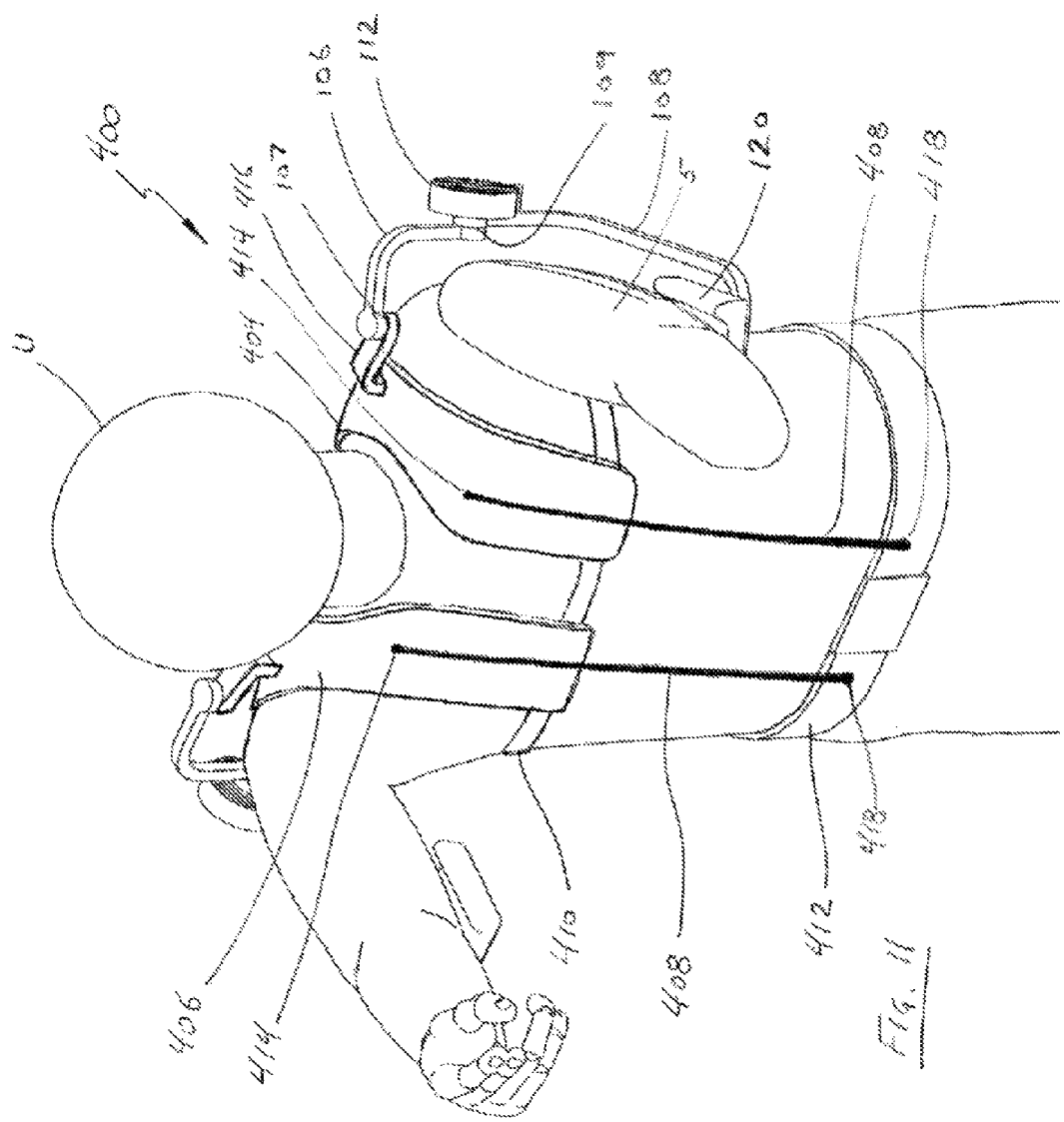

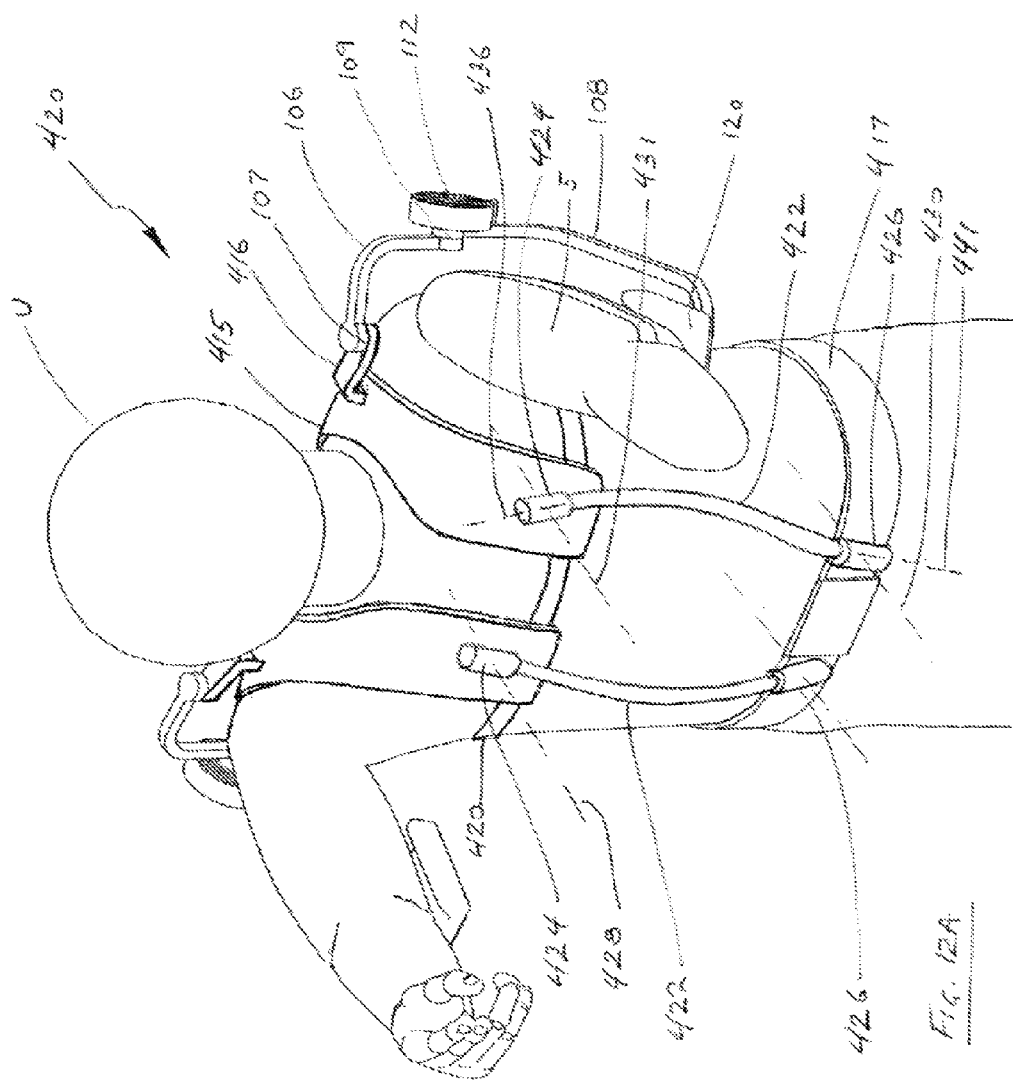

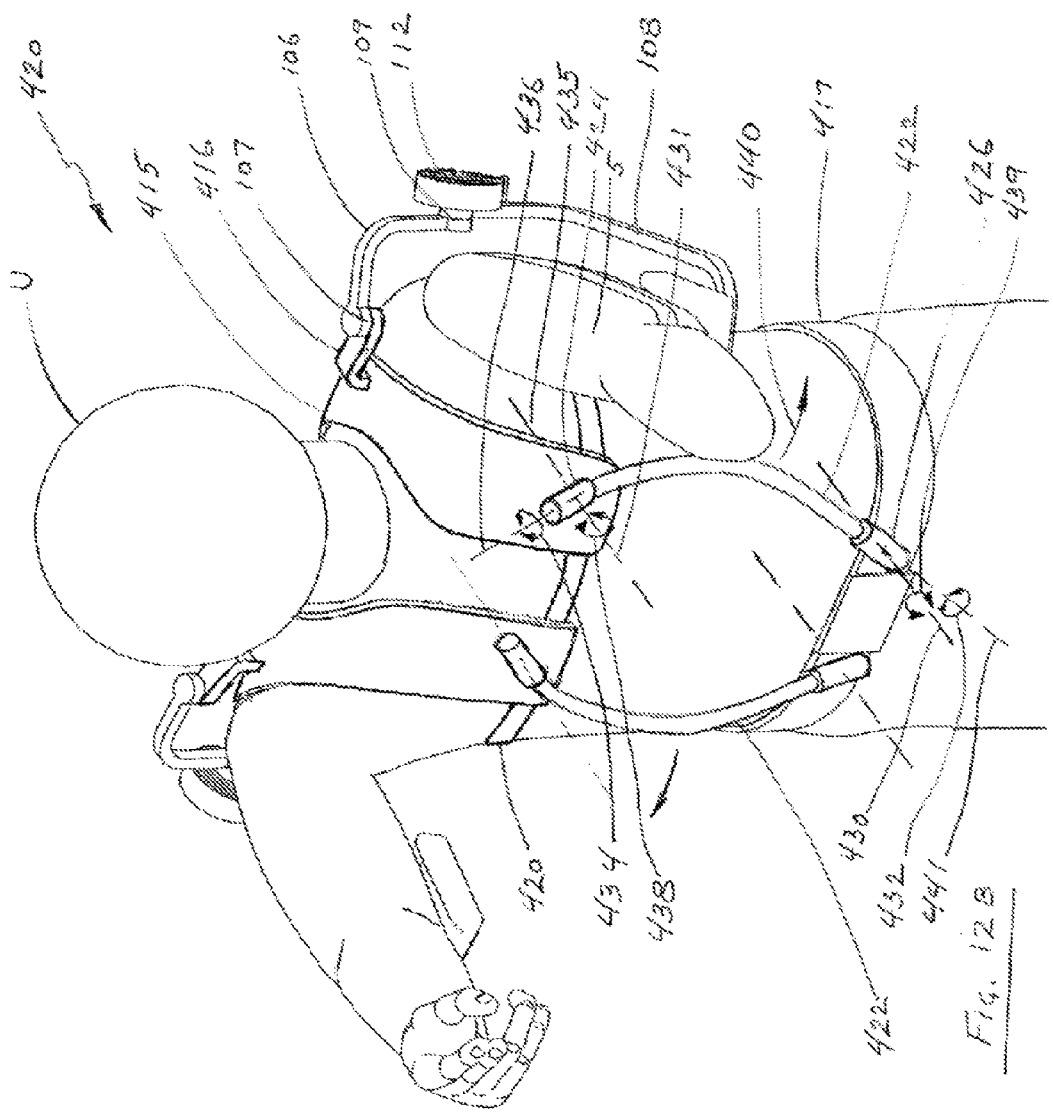

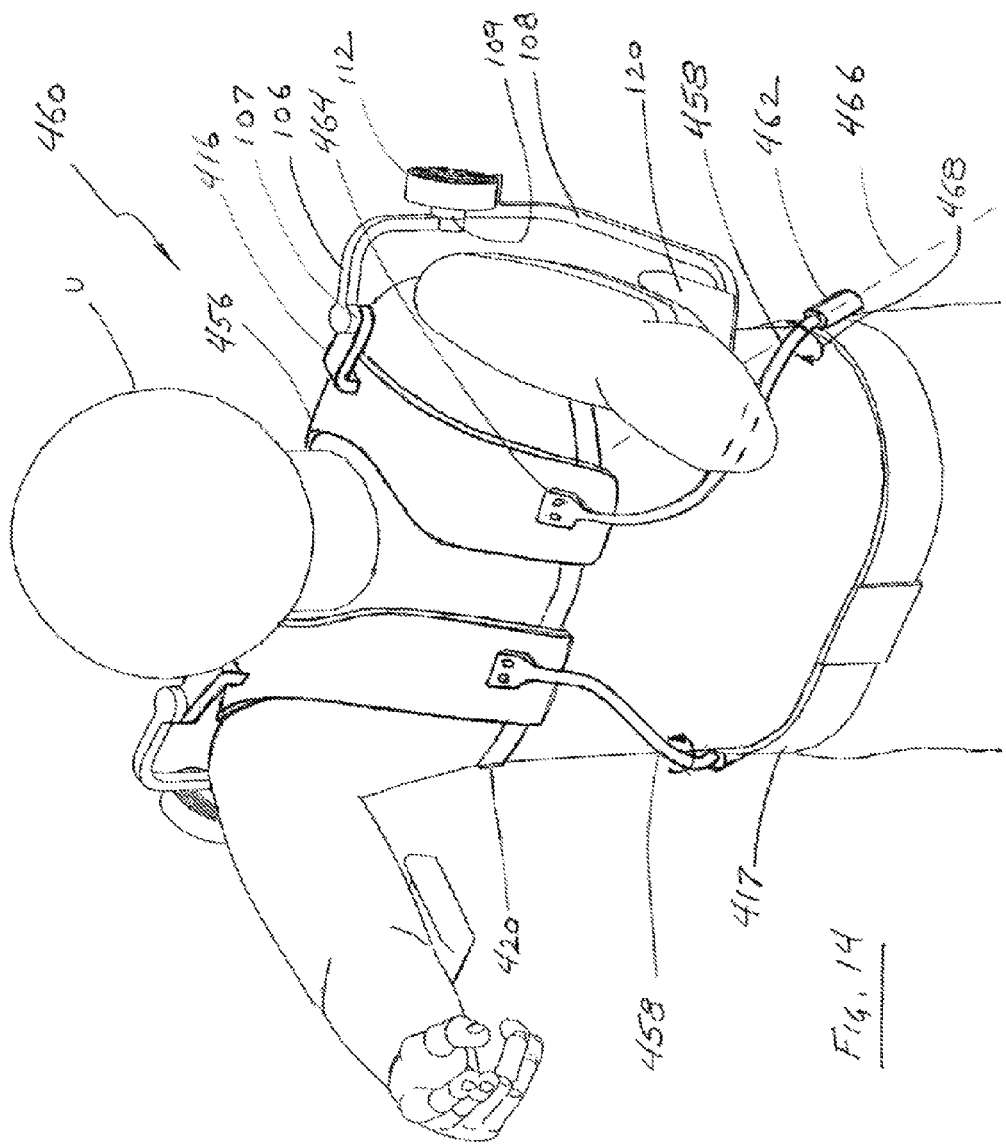

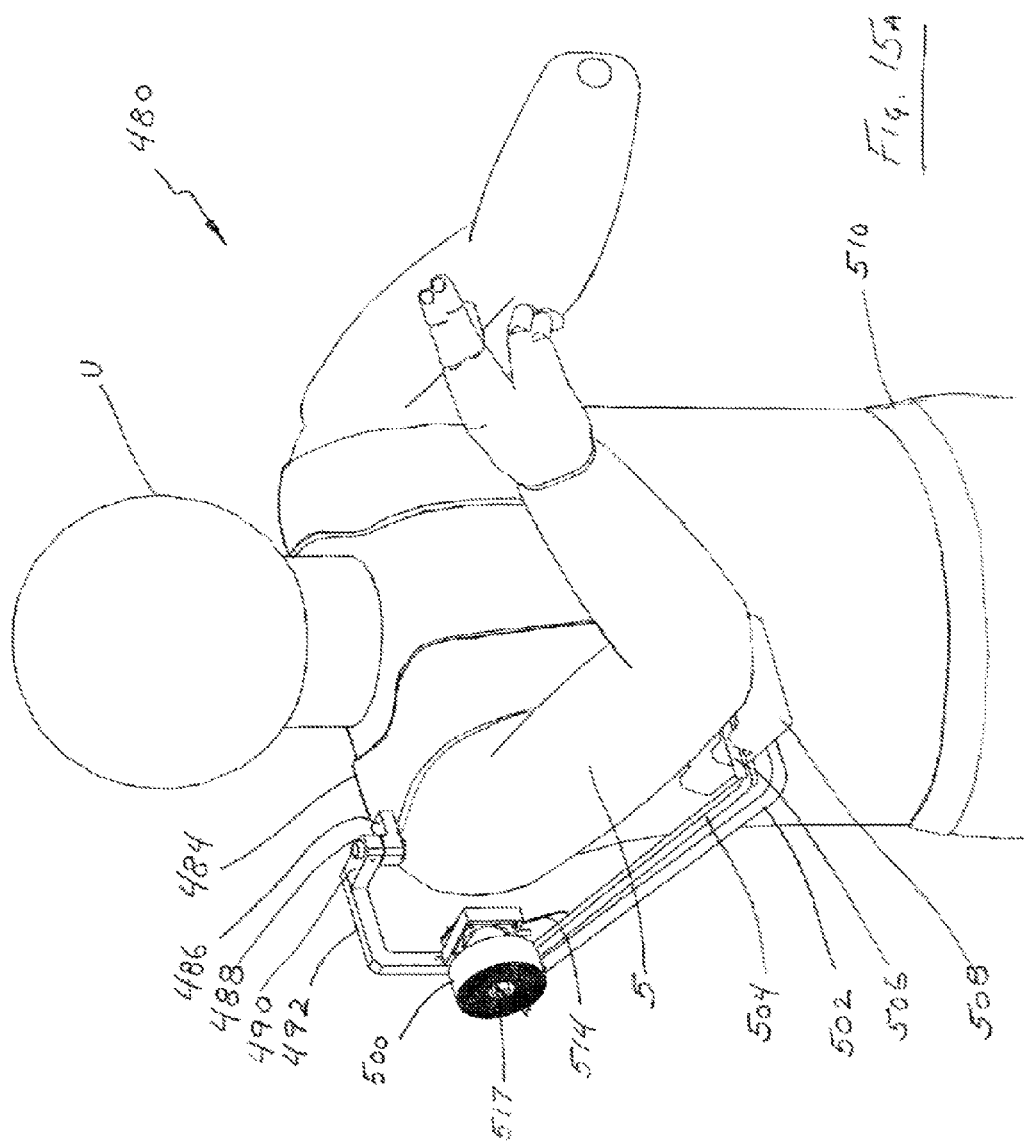

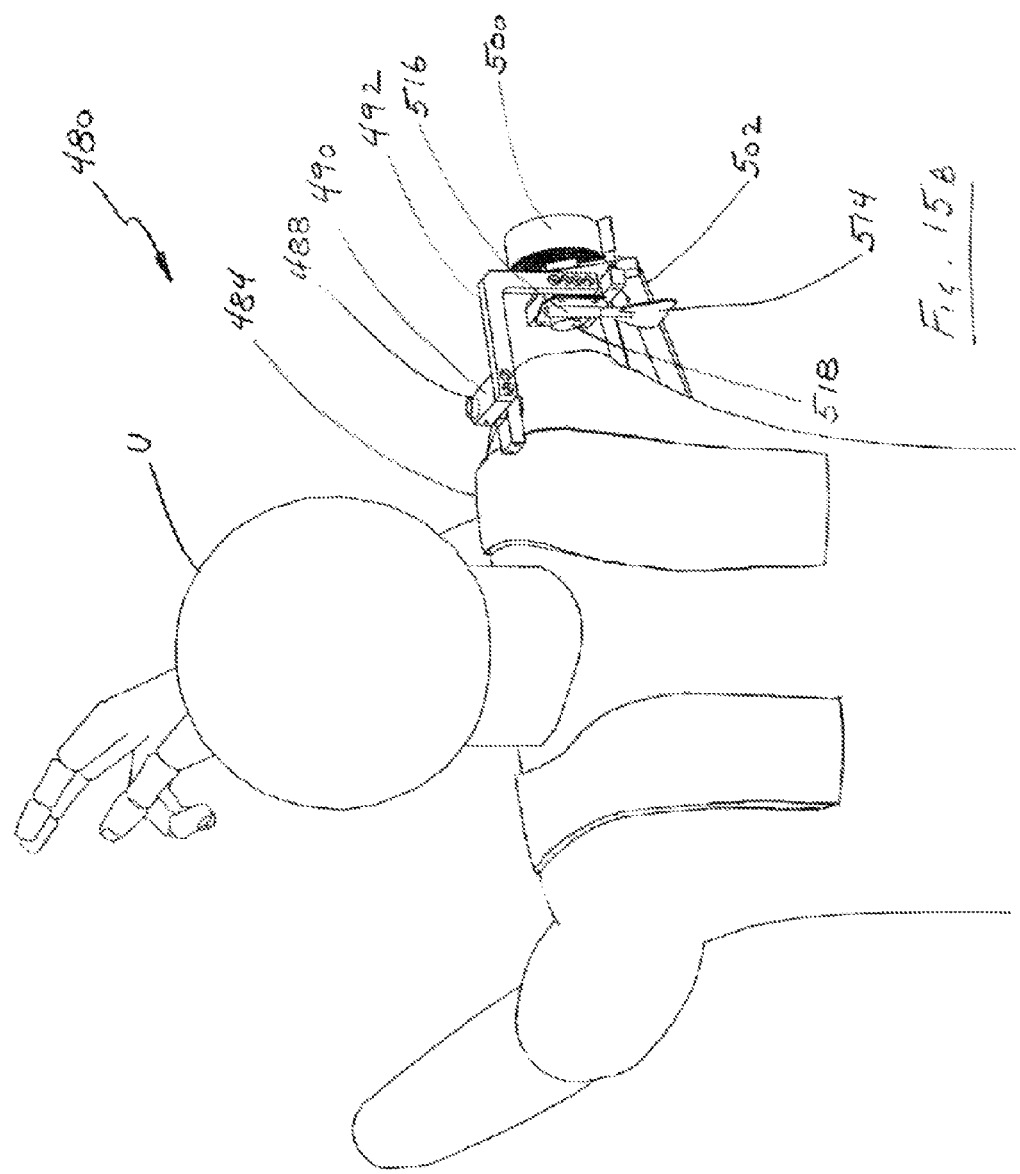

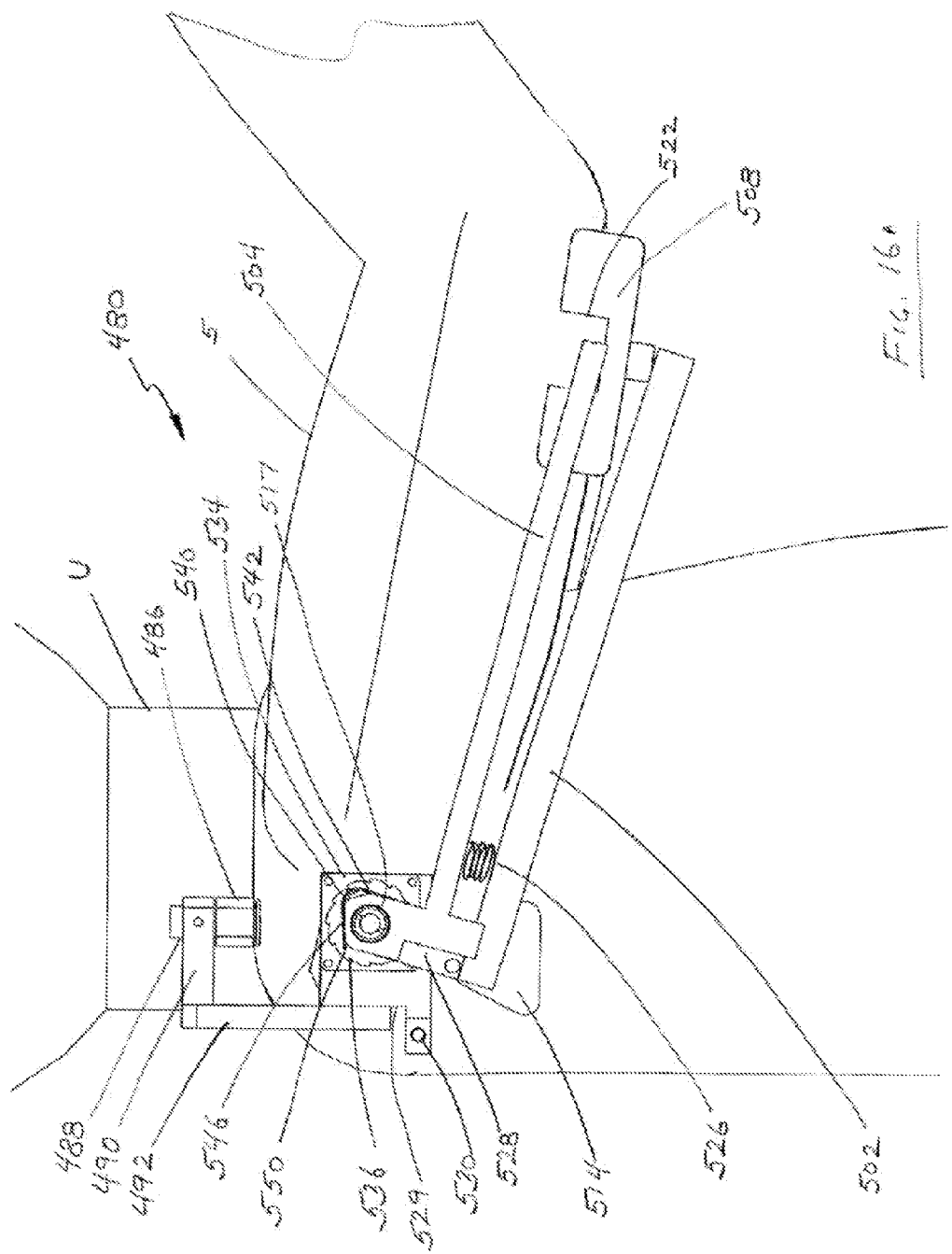

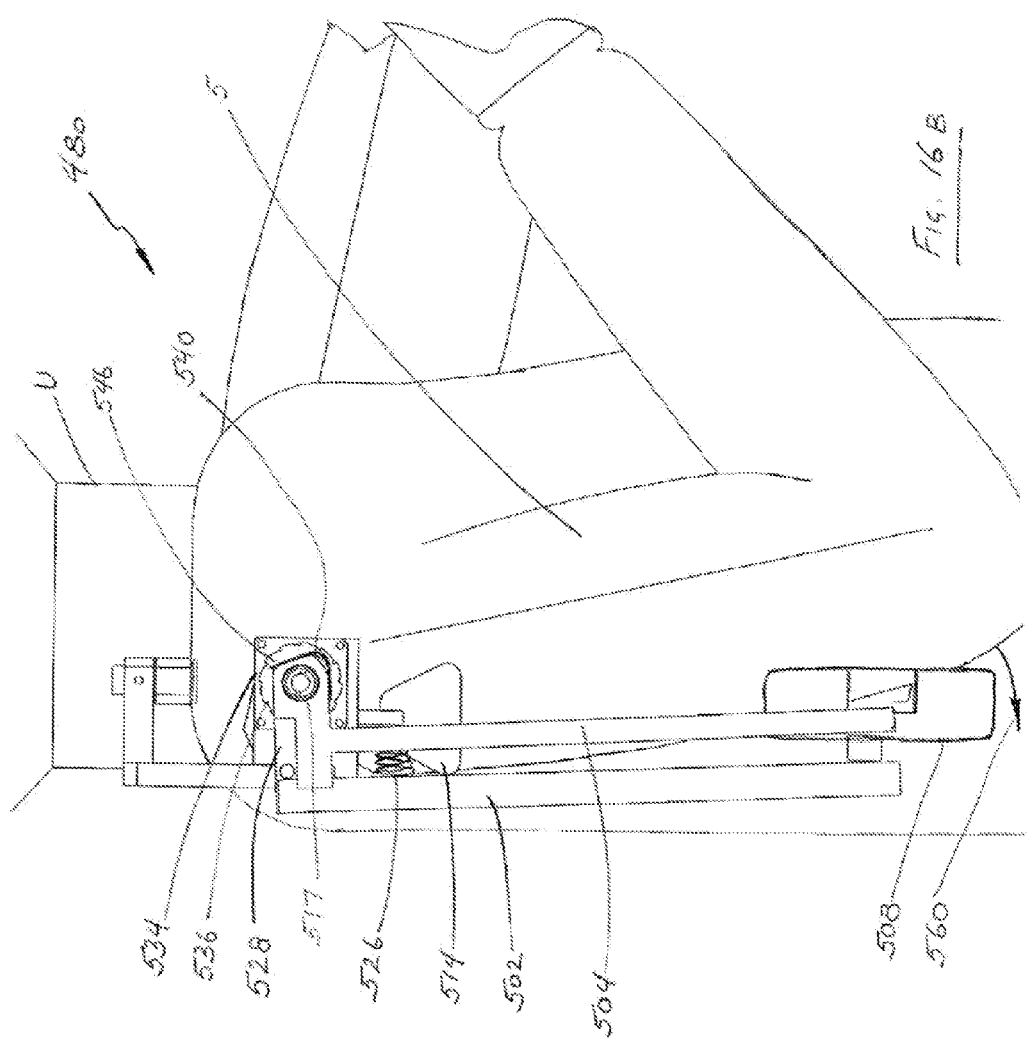

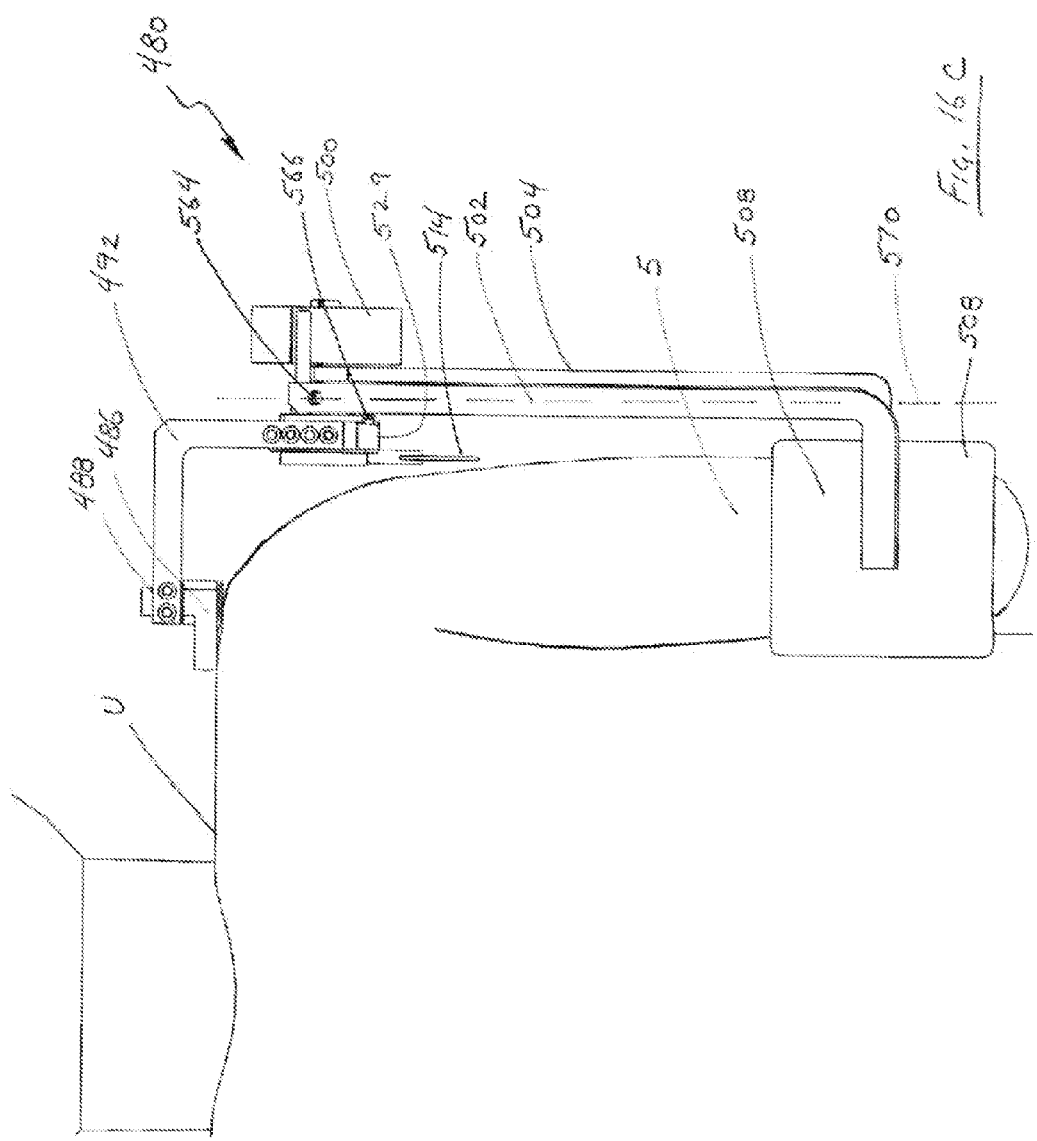

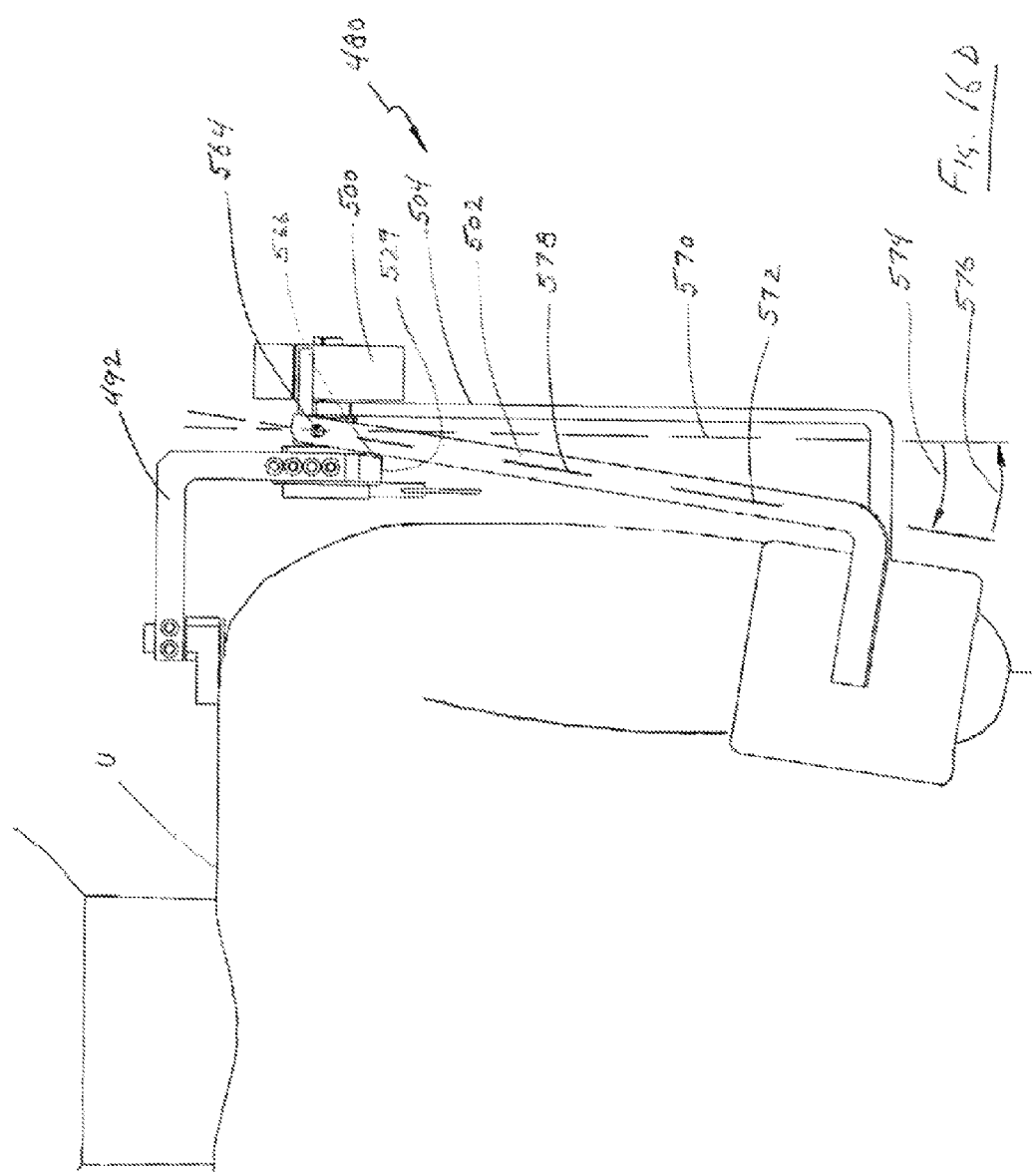

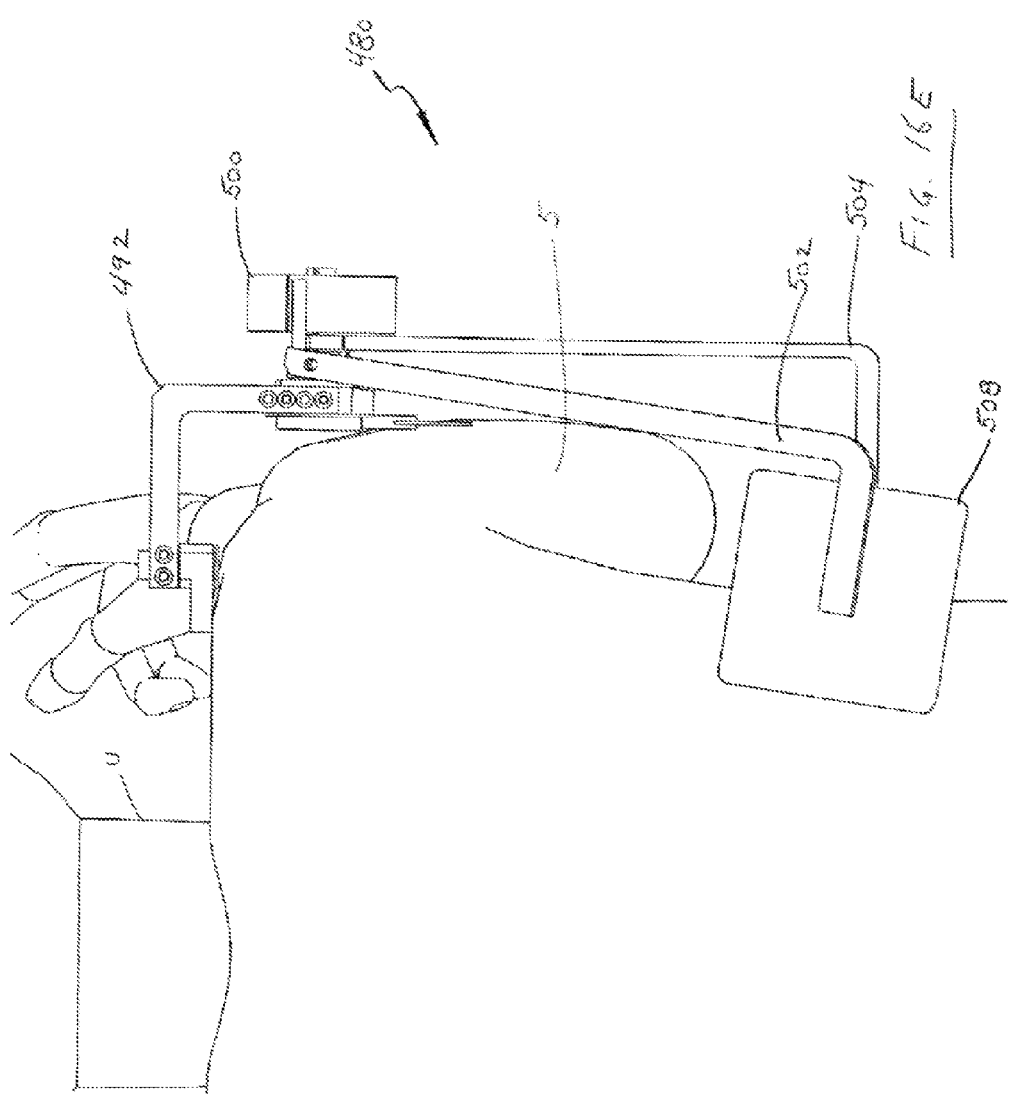

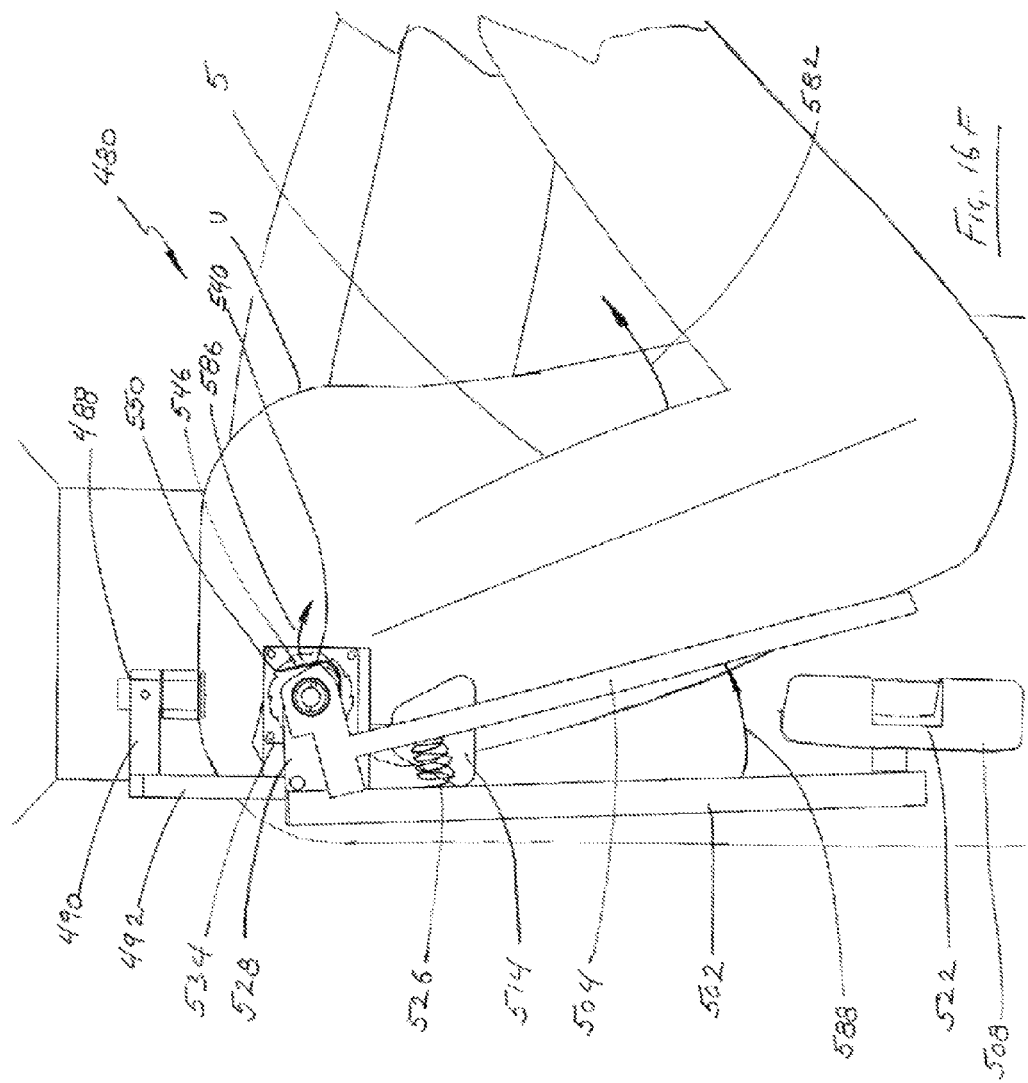

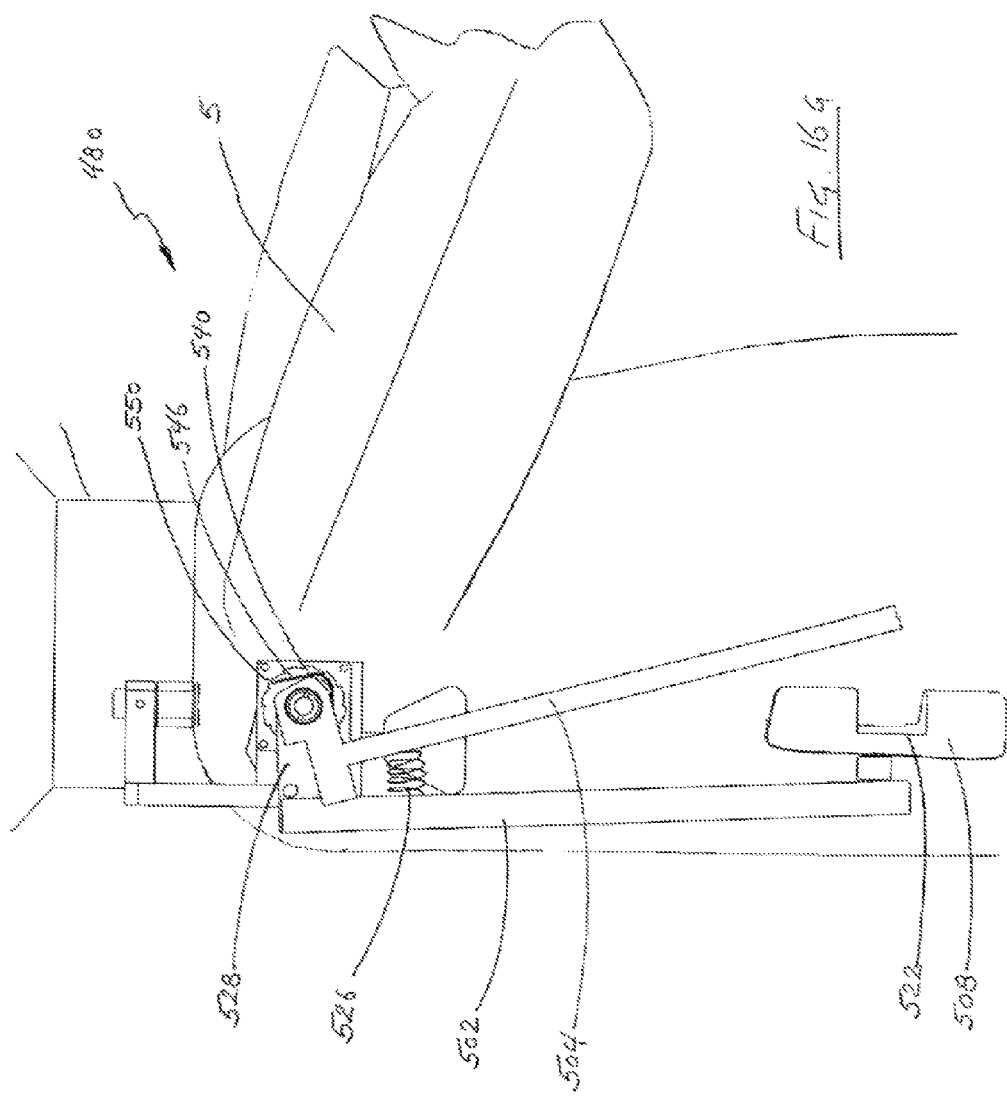

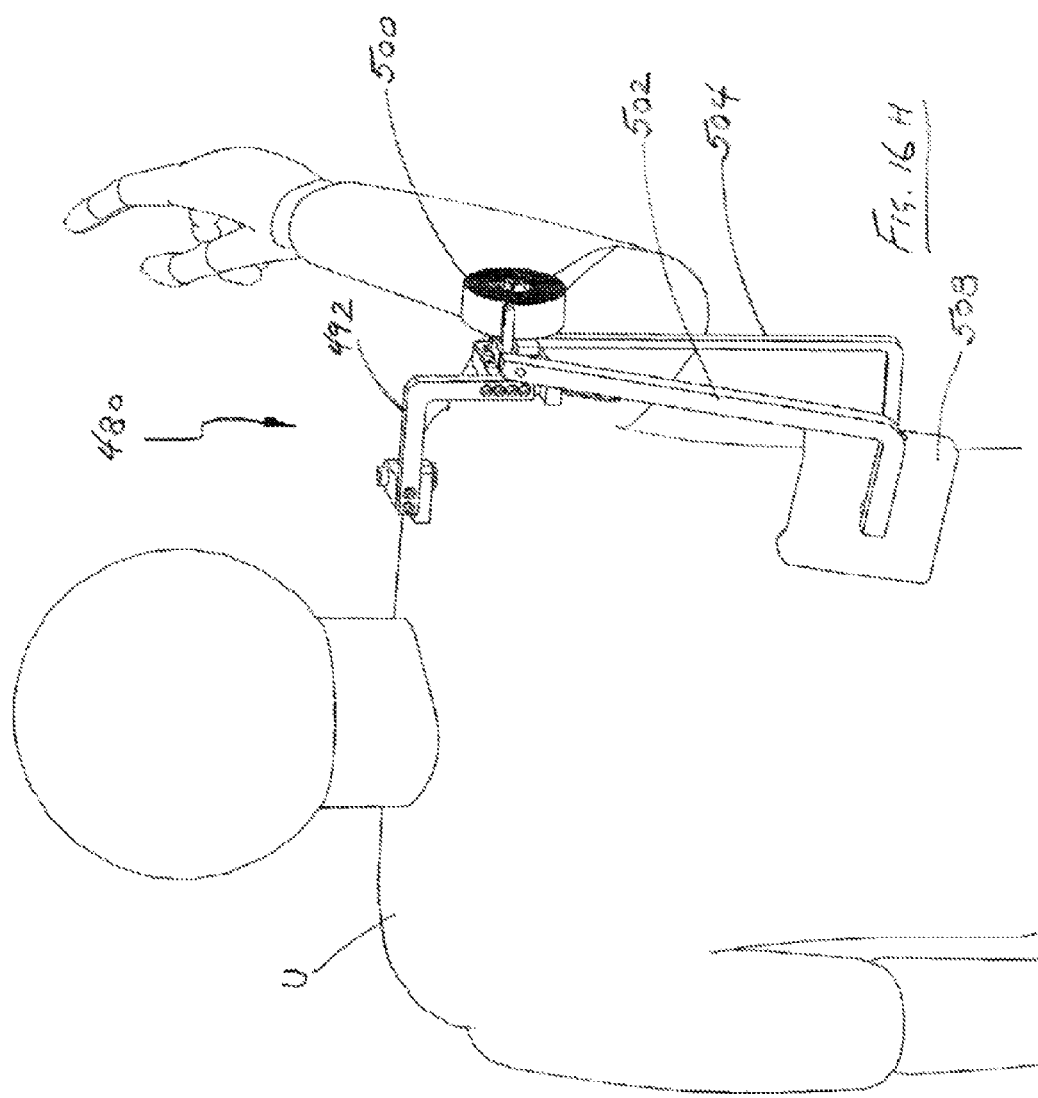

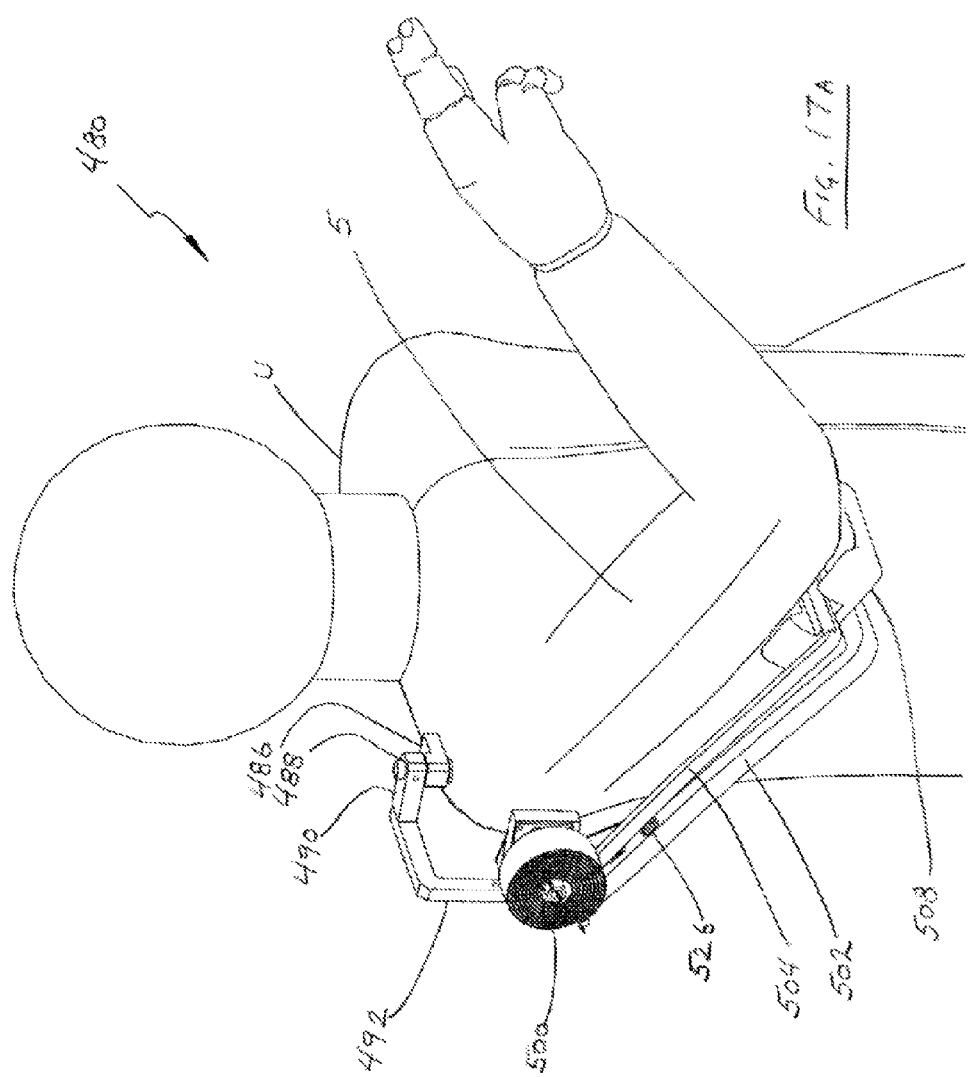

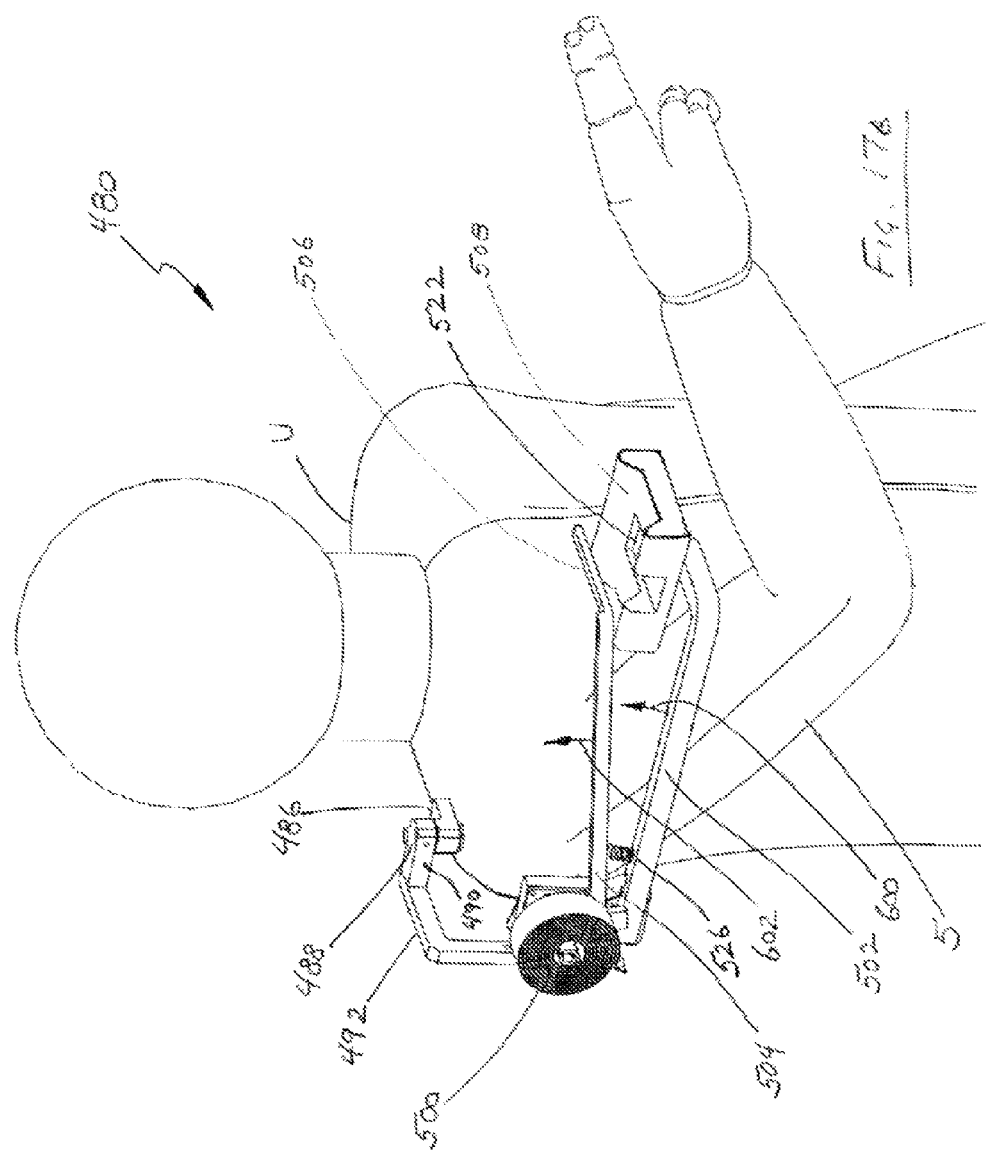

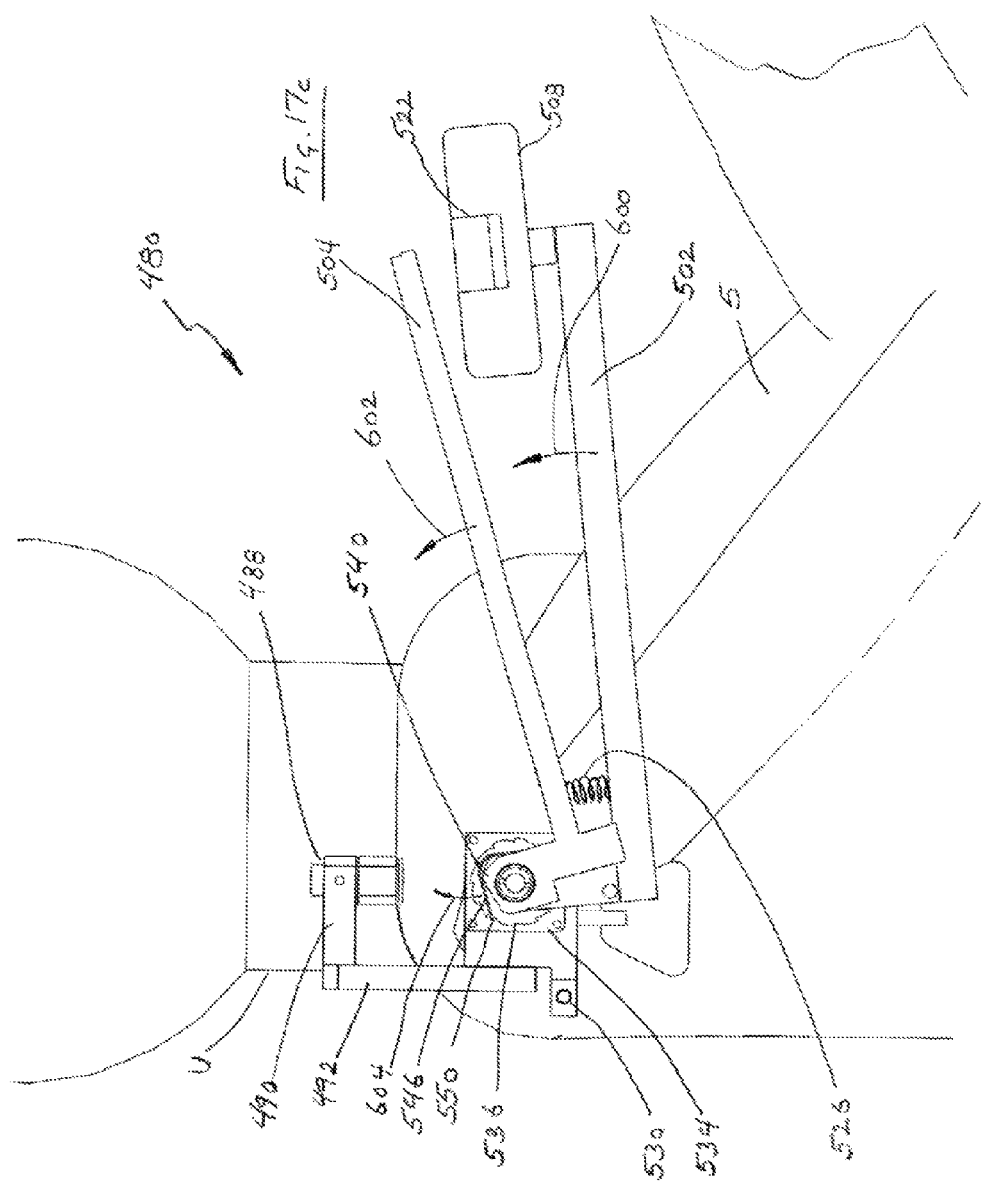

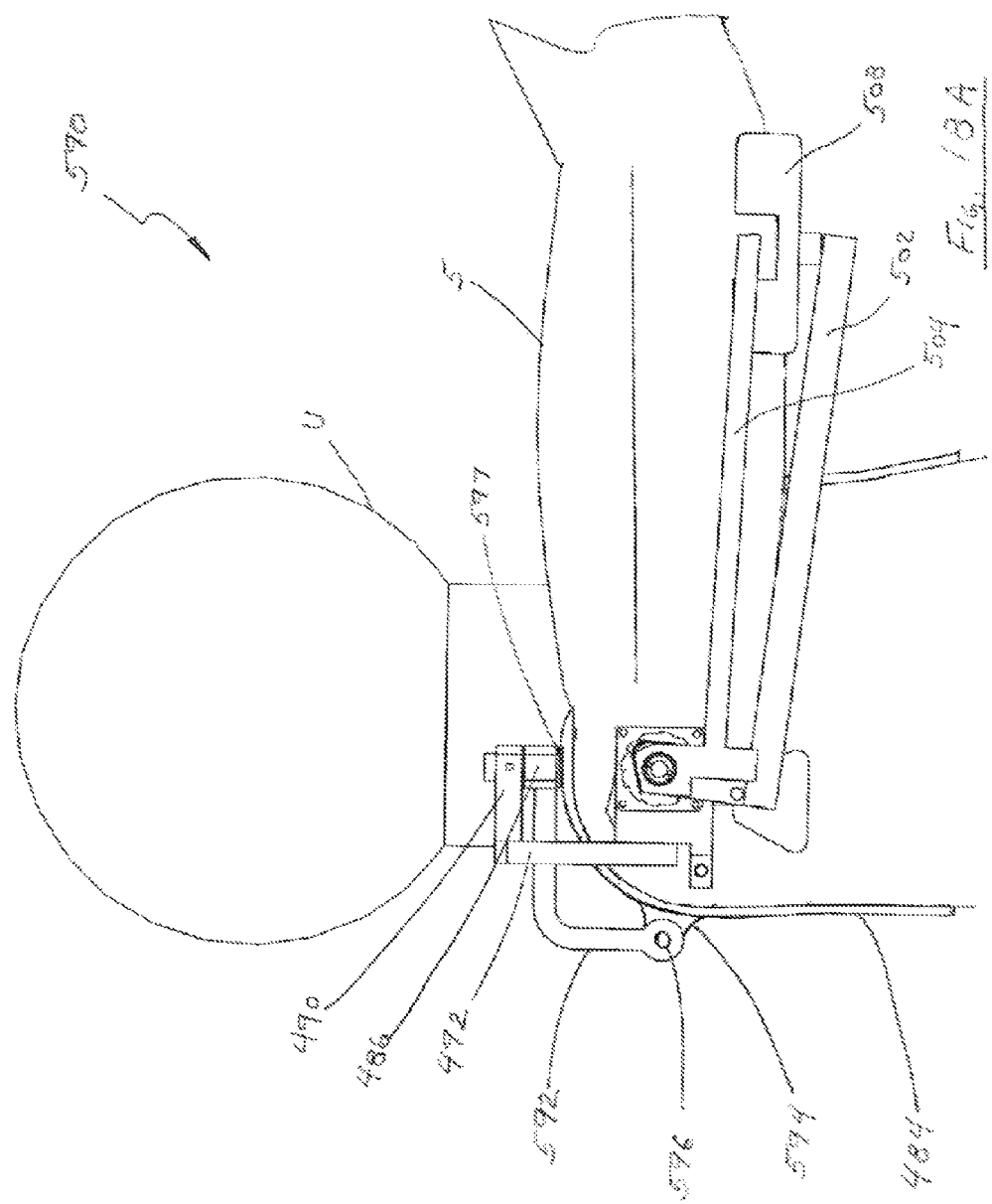

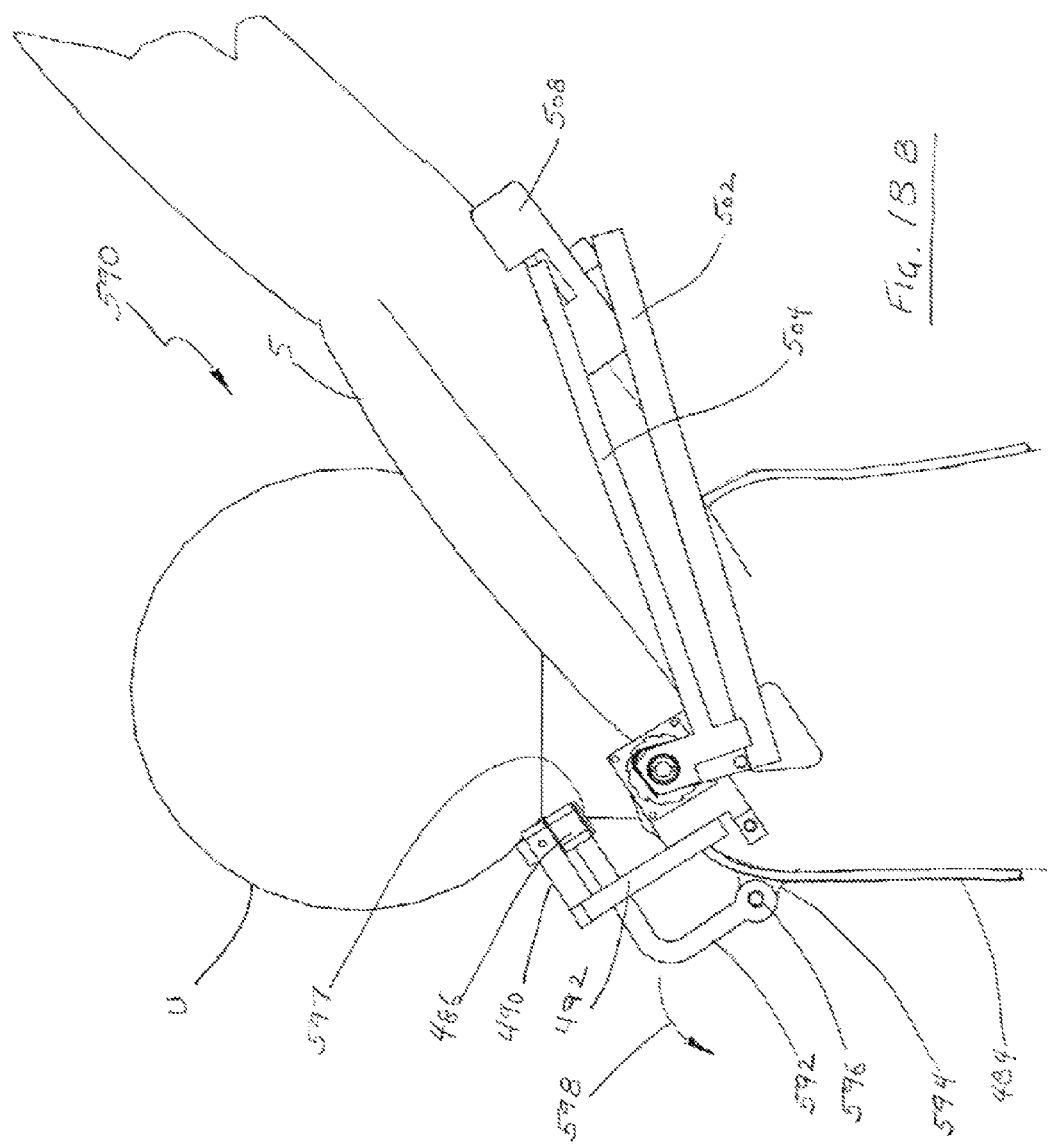
Fig. 18.B

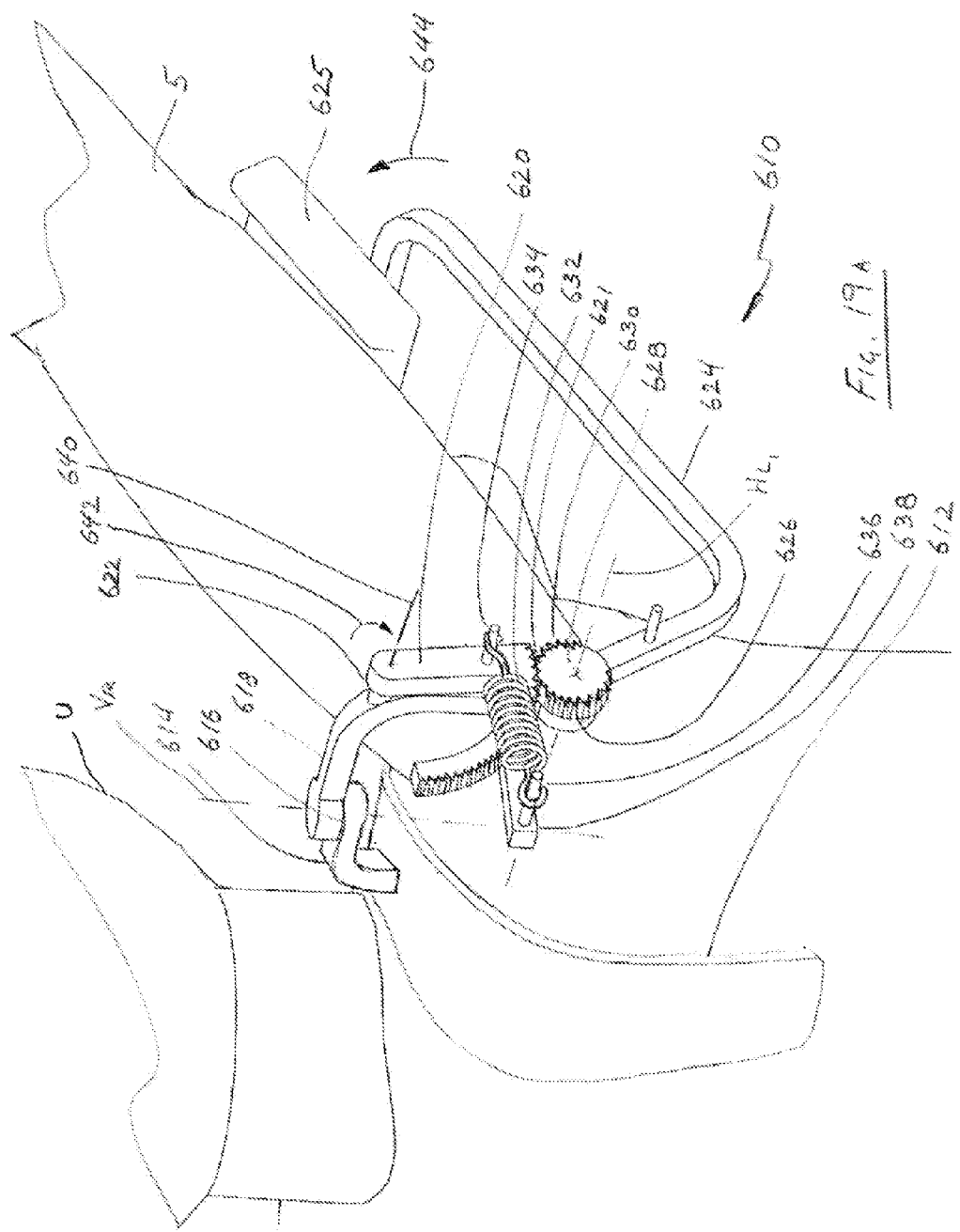

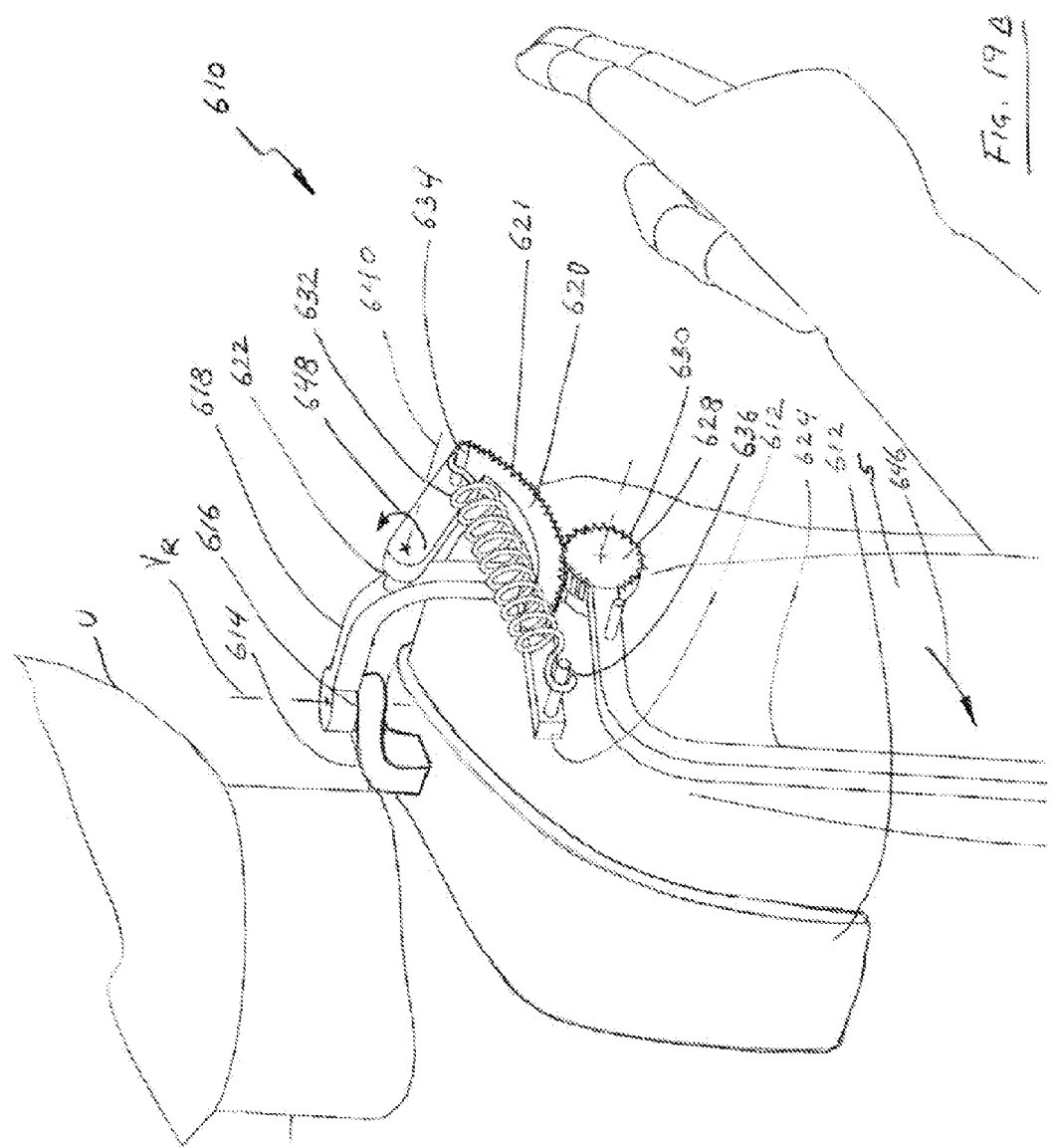

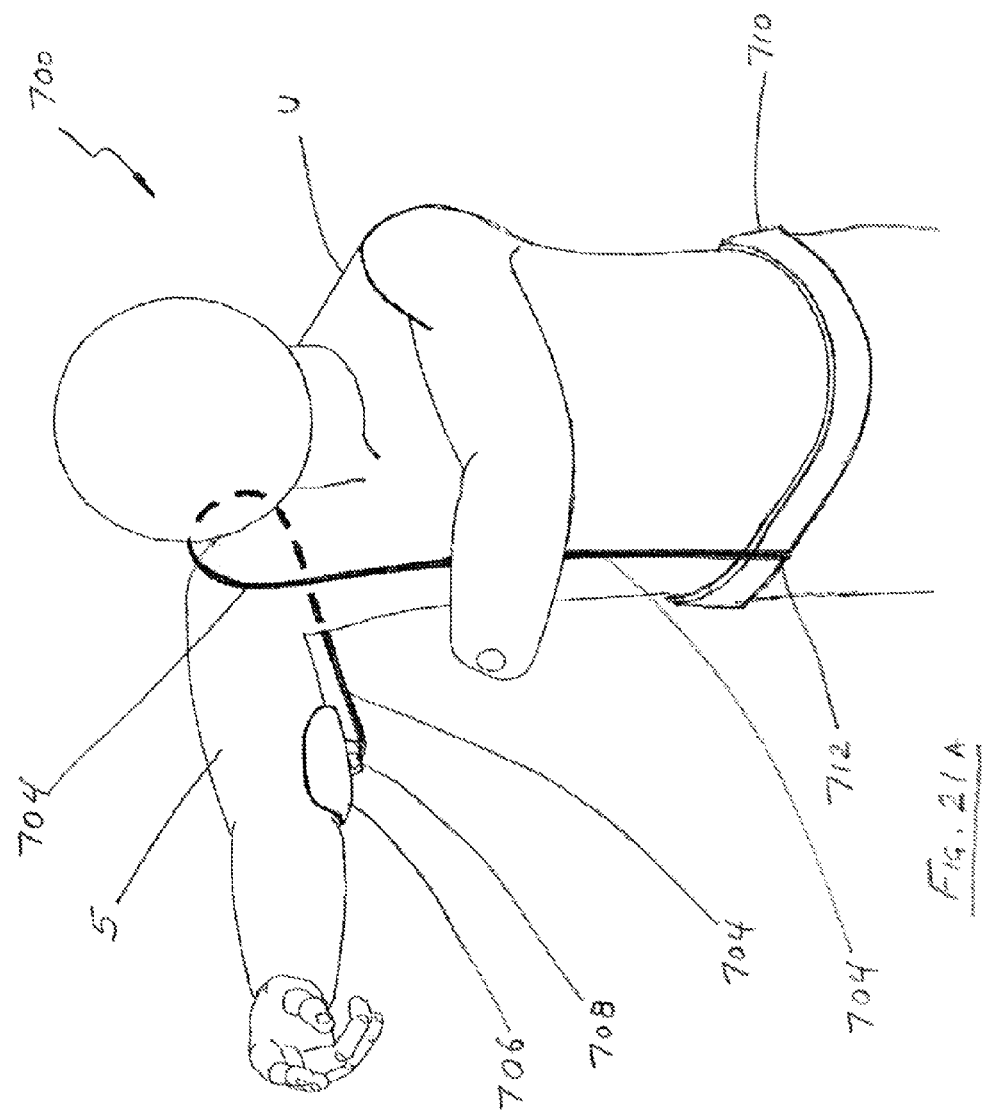

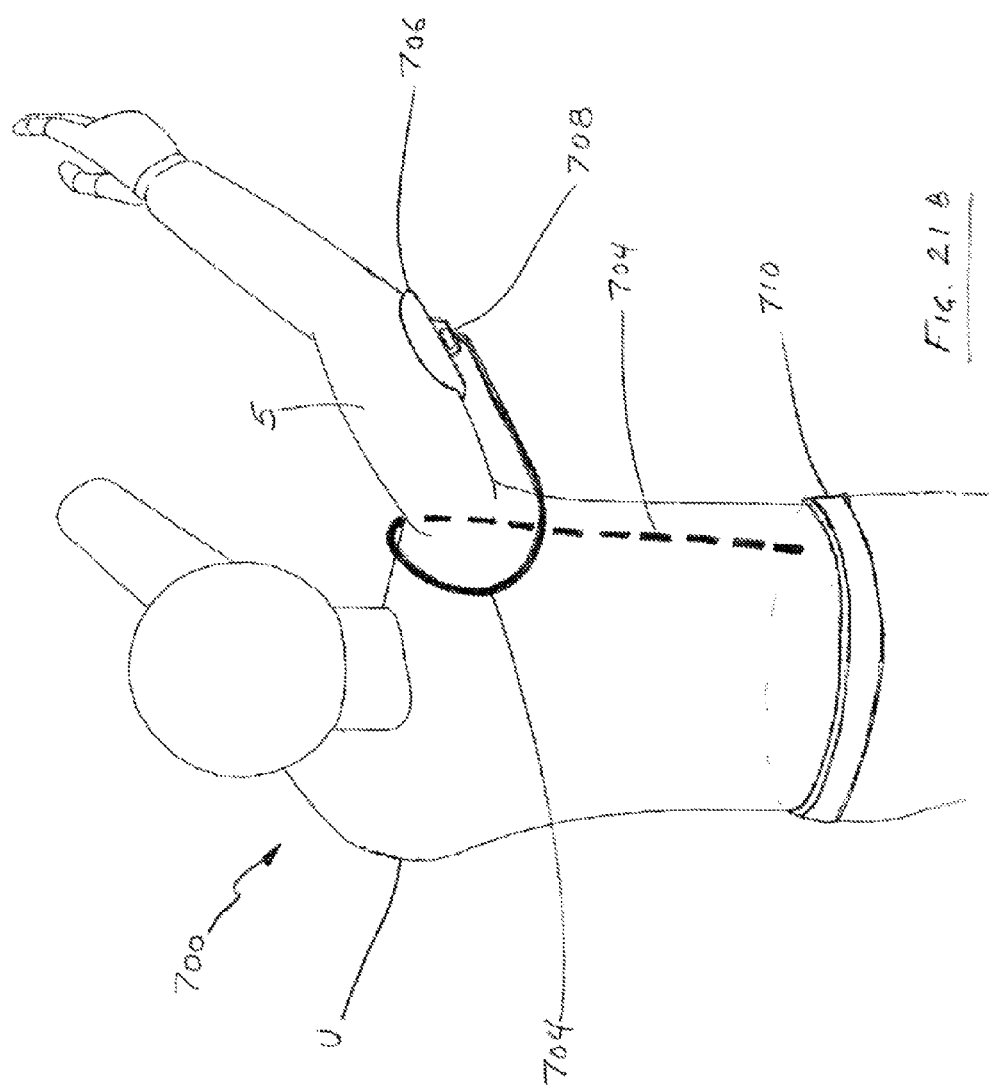

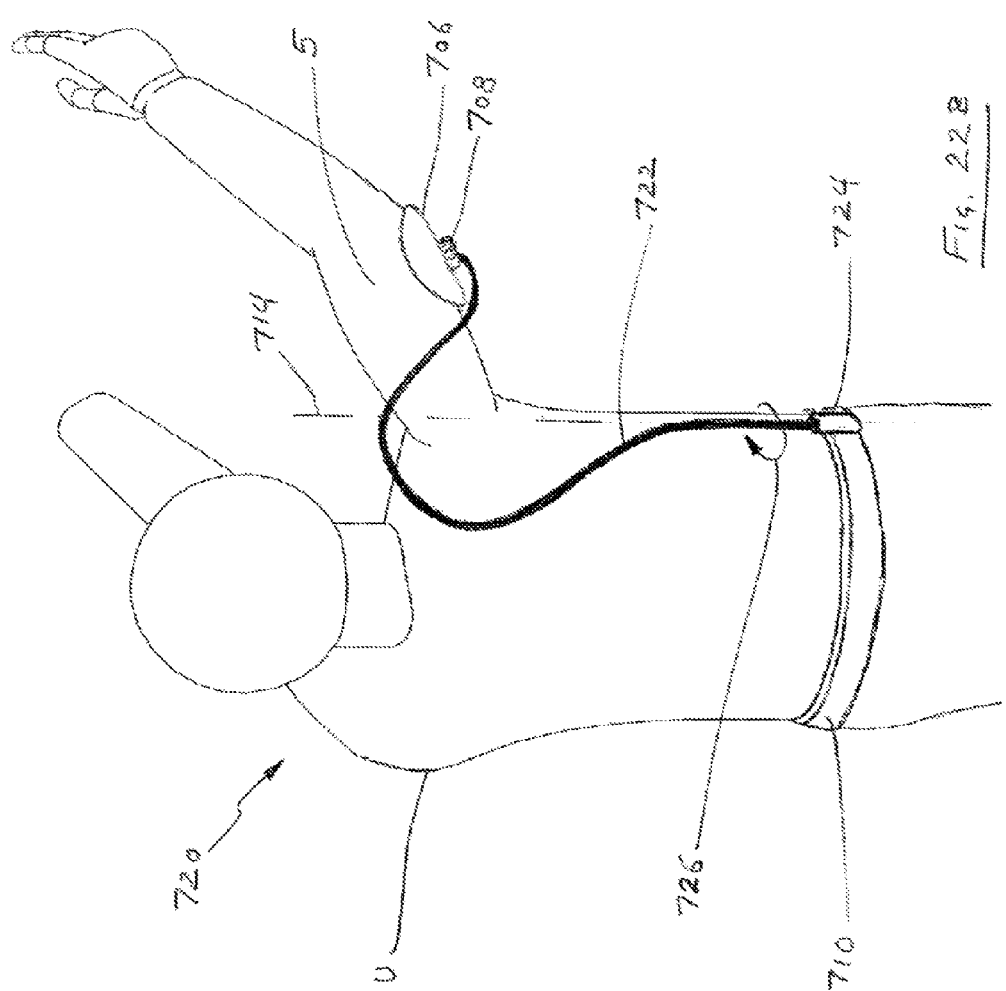

ADAPTIVE ARM SUPPORT SYSTEMS AND METHODS FOR USE

RELATED APPLICATION DATA

This application claims benefit of provisional applications Ser. Nos. 61/433,840, filed Jan. 18, 2011, and 61/507,535, filed Jul. 13, 2011, the entire disclosures of which are expressly incorporated by reference herein.

FIELD OF THE INVENTION

The present invention relates to systems, devices, and methods for supporting a user's arms, for example, to adaptive arm support systems that support one or both of a user's arms, while allowing substantially free motion, e.g., to allow the user to perform one or more tasks for extended periods of time with one or both arms extended.

BACKGROUND

Numerous tasks require people to work with their arms outstretched. Examples include surgery, dentistry, painting, dishwashing, and product assembly. Persons engaged in such activities may experience fatigue from prolonged muscular efforts required to resist the force of gravity on their arms in order to keep them extended. Weak or disabled persons may experience fatigue performing daily tasks. Static arm rests on chairs and work tables are only effective if the task is performed within a relatively restricted area, for example, at a computer keyboard. Tasks that involve a greater range of motion are not aided by static armrests.

Thus, there is a need for an adaptive armrest or arm support system that may relieve fatigue experienced by persons performing tasks involving moderate to large ranges of motion.

SUMMARY

The present invention is directed to systems, devices, and methods for supporting a user's arms, for example, to adaptive arm support systems or devices that support one or both of a user's arms, while allowing substantially free motion, e.g., to allow the user to perform one or more tasks for extended periods of time with one or both arms extended.

In accordance with one embodiment, an apparatus or system is provided for supporting an arm of a user that includes a harness configured to be worn on a torso of a user; and an arm support coupled to the harness and configured to support a portion of an arm of the user, the arm support configured to accommodate movement of the arm while following the movement without substantially interfering with the movement. The arm support may be configured to at least partially offset a gravitational force acting on the arm as the user moves and the arm support follows the movement of the user's arm. For example, the arm support may transfer at least a portion of the weight of the user's arm to the torso or other region of the user's body and/or may apply an opposing force to at least partially offset the gravitational force acting on the arm.

In one embodiment, the system includes one or more compensation elements coupled to the arm support to at least partially offset a gravitational force acting on the arm as the user moves and the arm support follows the movement of the user's arm. For example, the compensation element(s) may include one or more springs coupled to the arm support to at least partially offset the gravitational force acting on the arm of the user as the user moves without substantially interfering with movement of the user's arm. Alternatively, the compensation element(s) may include an electric, hydraulic, or pneumatic system coupled to the arm support to apply forces to the arm support to at least partially offset the gravitational force acting on the arm. In this alternative, the compensation element(s) may include one or more sensors for detecting an orientation of the arm support to determine a component of gravitational force acting on the user's arm, and one or more actuators for applying a force to at least partially offset the component of gravitational force.

In accordance with another embodiment, an apparatus or system is provided for supporting an arm of a user that includes a harness configured to be worn on a torso of a user, the harness defining a vertical axis extending generally parallel to a spine of the user wearing the harness. An arm support may be coupled to the harness and including an arm rest configured to support a portion of an arm of the user, the support rotatable about a vertical pivot point generally parallel to the vertical axis and about a horizontal pivot point generally orthogonal to the vertical axis without substantially interfering in movement of the user's arm while the user's arm received in the arm rest. One or more compensation elements may be coupled to the arm support to at least partially offset a gravitational force acting on the arm of the user as the user moves and the arm support follows the user's movement.

Optionally, a pair of arm supports and associated compensation elements may be coupled to the harness for supporting both arms of the user.

In accordance with still another embodiment, a method is provided for supporting an arm of a user during one or more tasks. A harness may be placed on the user, the harness comprising an arm support movable relative to the harness and including an arm rest. A portion of the user's arm may be supported using the arm rest such that the arm support subsequently follows movement of the user's arm. The user may then perform one or more tasks involving movement of the user's arm, the arm support at least partially offsetting a gravitational force acting on the user's arm during the movement without substantially interfering in the movement.

Thus, the devices, systems, and methods herein may counterbalance all or part of the weight of one or both of a user's arms as the user performs one or more tasks, which may reduce arm and/or shoulder muscle fatigue. In addition or alternatively, the arm support systems herein may adaptively reposition with the user, e.g., following movement of the user's arms as the user performs normal tasks without substantially interfering with the tasks. For example, the weight of one or both of the user's arms may be transmitted into the harness via a system of arm rests, links, pivots, and/or energy sources, such as springs. Thus, with the harness worn or otherwise attached to the user, the system may transmit at least a portion of the weight of the user's arm(s) to the user's abdomen, shoulder, hips, sides, or other regions of the user's torso, which may be more readily adapted to receive and resist such forces without undue muscle fatigue and/or discomfort.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIGS. 3A and 3B show a top view of a body-mountable adaptive arm support system with different arm rotations about a vertical pivot axis.

FIGS. 4A-4C show side views of a body-mountable adaptive arm support system with different arm rotations about a horizontal pivot axis.

FIG. 4D is a detail of the torque element of FIG. 4C.

FIGS. 7A and 7B show front and rear views, respectively, of the body-mountable adaptive arm support system of FIGS. 6A and 6B removed from the user.

FIG. 9 shows a front perspective view of a body-mountable adaptive arm support system, similar to that of FIGS. 2-5, with one side disabled.

FIG. 10 shows a rear perspective view of yet another embodiment of a body-mountable adaptive arm support system, similar to that of FIGS. 2-5 yet configured for only one arm.

FIG. 11 shows a front perspective view of still another embodiment of a body-mountable adaptive arm support system.

FIGS. 12A and 12B show front perspective views of another embodiment of a body-mountable adaptive arm support system.

FIGS. 13 and 14 show front perspective views of additional embodiments of a body-mountable adaptive arm support system.

FIGS. 15A and 15B show front and rear perspective views, respectively, of another embodiment of a body-mountable adaptive arm support system including a mechanism for adjusting a torque element of the system.

FIGS. 16A through 17C show an exemplary embodiment of lock-out, brake, or other safety features that may be provided on any of the support systems herein.

FIGS. 18A and 18B show side views of another exemplary embodiment of a support system include features to facilitate lifting the user's arm overhead.

FIGS. 19A through 22B show various embodiments of features that may provide a compensation force for any of the support systems herein.

DETAILED DESCRIPTION

Figure 1:
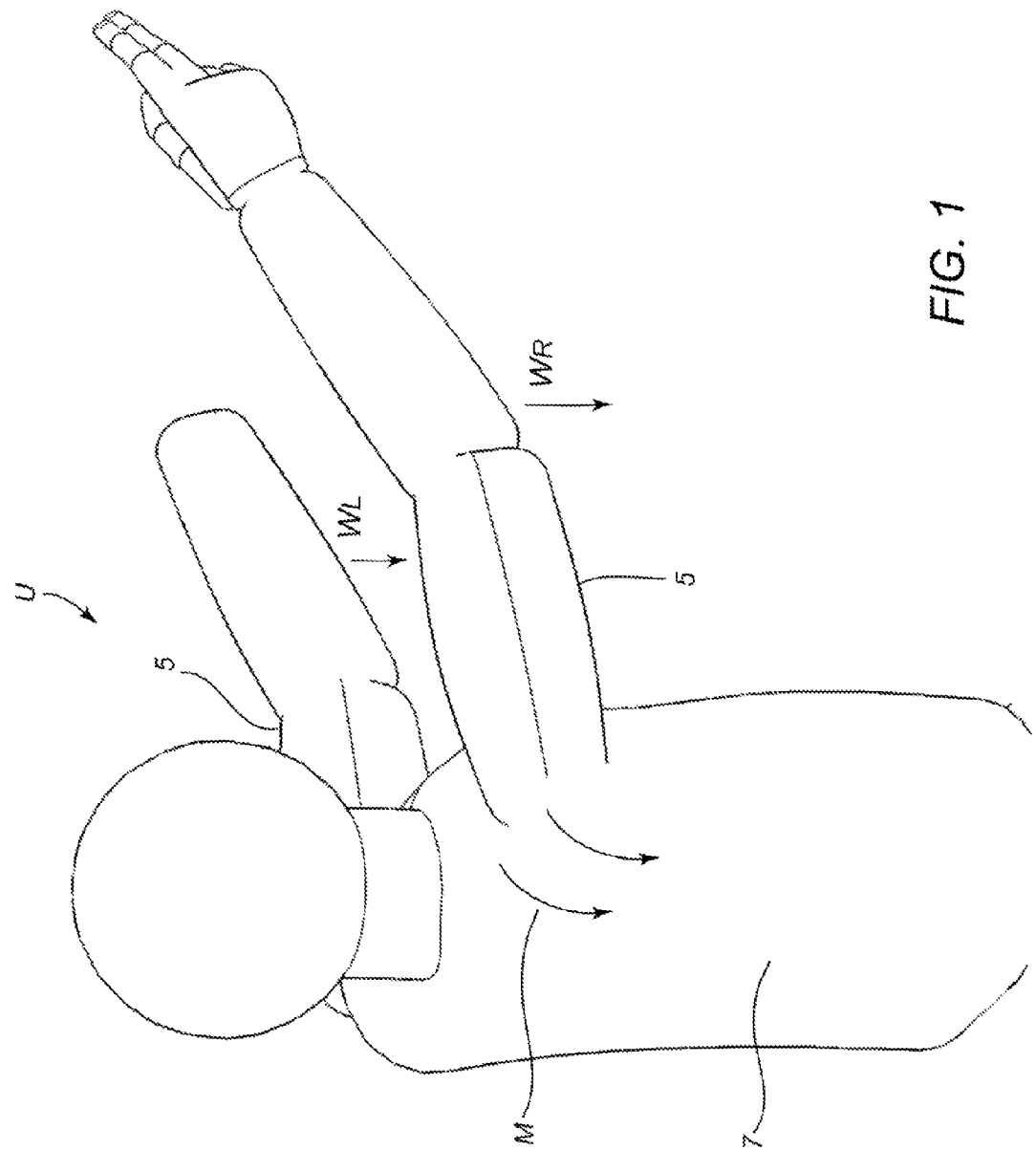
FIG. 1 is a perspective view of a person with arms outstretched.

Persons performing tasks with one or both of their arms outstretched for long periods of time may experience fatigue. As shown in FIG. 1, the force of gravity Wl and Wr on the outstretched arms 5 of a user U must be resisted by the user's shoulder and back muscles M. Over long periods, this may result in fatigue, and a corresponding degradation in performance and accuracy. Surgeons, for example, may need to move and hold their arms partially or fully outstretched for long periods of time. Many report problems with fatigue, tremors, and reduced accuracy. In some cases, surgeons are unable to perform procedures daily, but instead have to rest for a day between operations. Static armrests, such as those commonly found on armchairs, provide arm support, but are effective only in a limited range of positions. Therefore, there is a need for an arm support system which supports the user's arms over a greater range of motions.

To address this need, the present application provides various adaptive arm support systems that support one or both of a user's arms, e.g., substantially vertically, while allowing substantially free motion of the arm(s), e.g., about multiple axes, to allow the user to perform one or more tasks for extended periods of time with the arm(s) extended.

As used herein, "vertical" generally means substantially vertical, i.e., along a vertical axis extending generally parallel to the spinal column of the user U. Thus, although the user U may generally stand substantially erect during activities while wearing the adaptive arm support systems herein, the user U may move in ways to skew the vertical axis off of true vertical. As used herein, "horizontal" generally means substantially horizontal, i.e., along a horizontal axis that extends orthogonally, e.g., substantially perpendicular, to the vertical axis extending generally parallel to the spinal column of the user U. For the example, the horizontal axis may extend generally parallel to an axis extending between the shoulders of the user U.

Figure 2A:
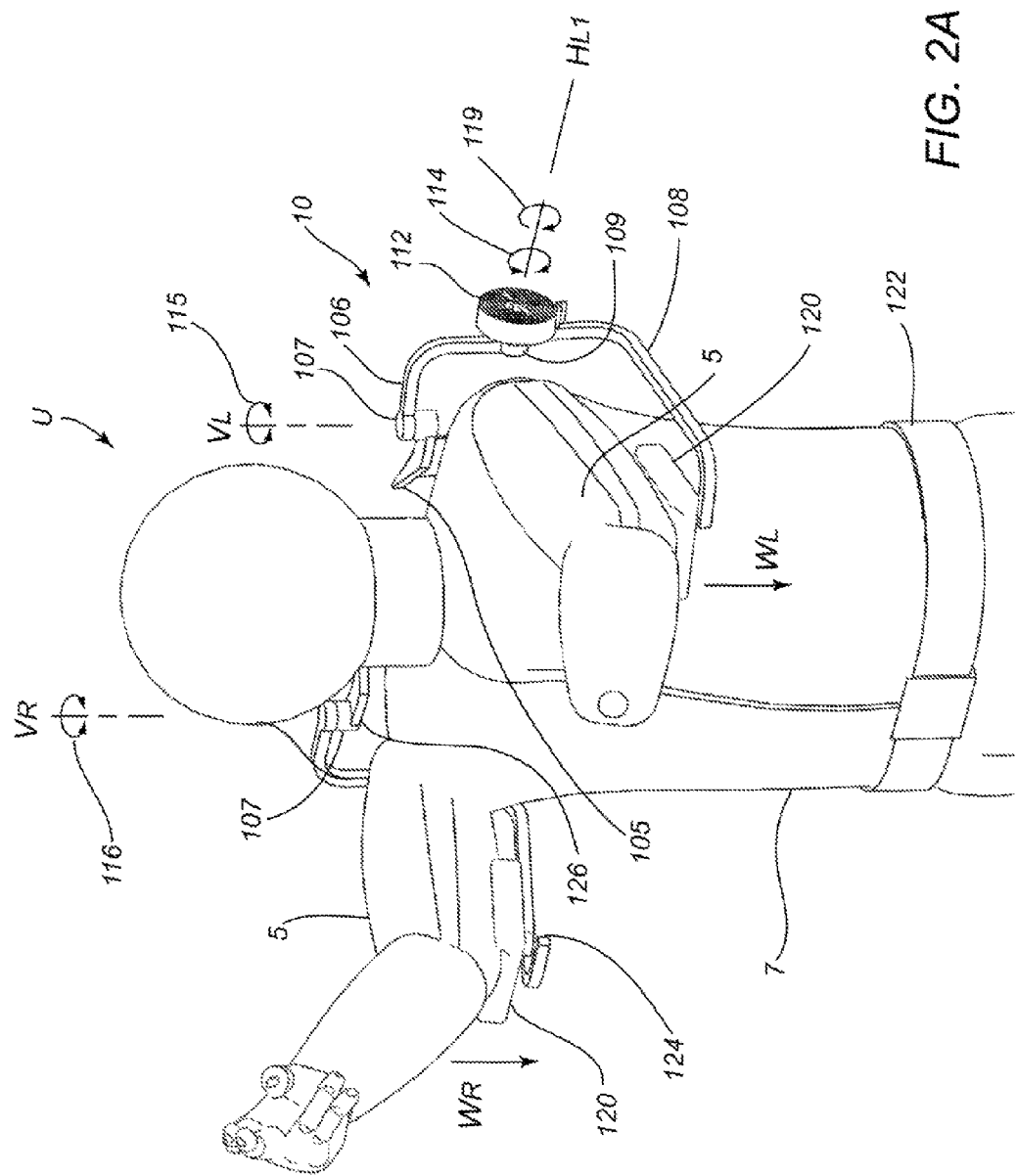
FIGS. 2A and 2B show front and rear perspective views, respectively, of an exemplary embodiment of a body-mounted adaptive arm support system worn by a user.
Figure 2B:
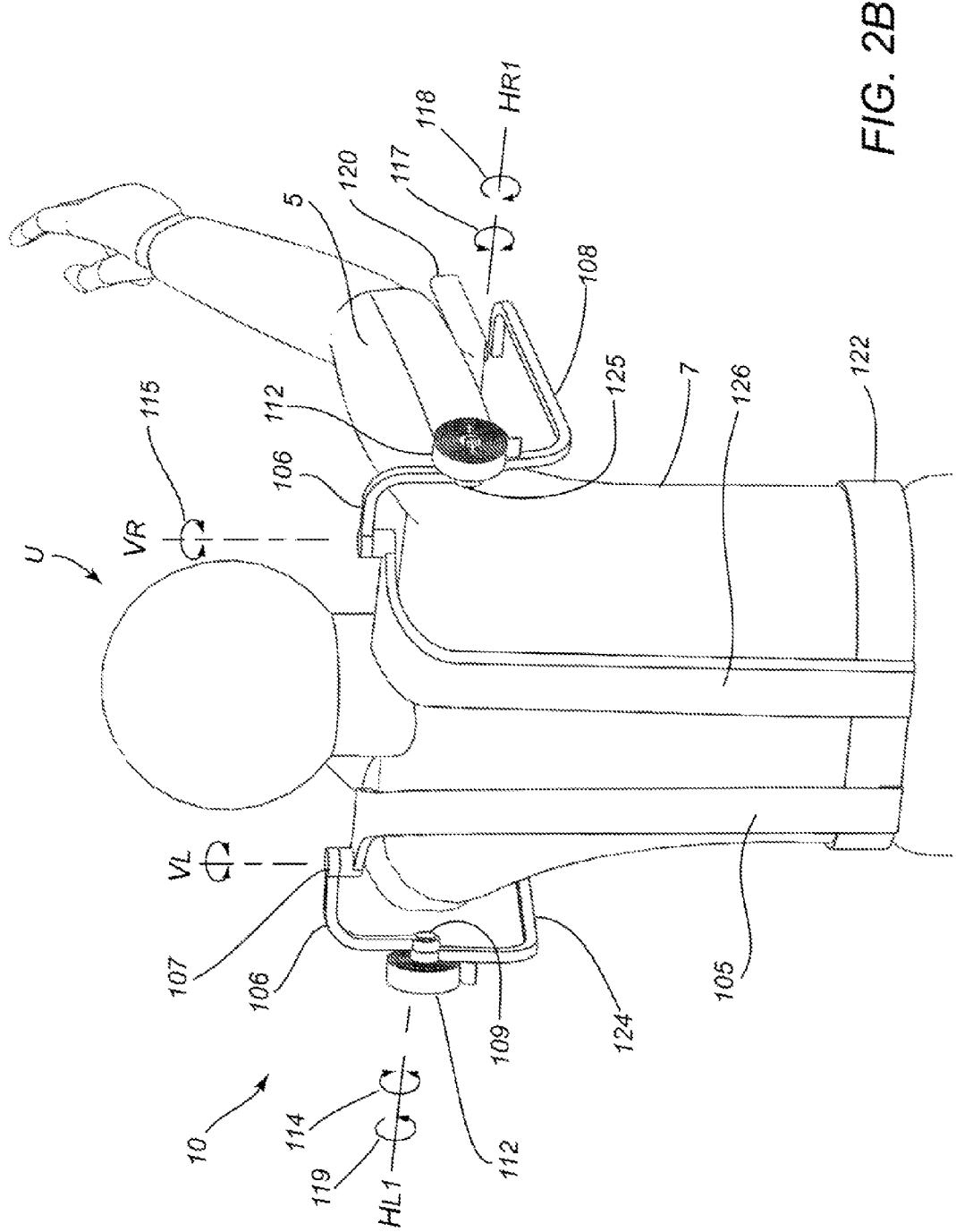

Turning to the drawings, FIGS. 2A and 2B show a user U wearing a first exemplary embodiment of an adaptive arm support system 10. Torso brackets 105, 126 are connected to attachment band 122, and together form a harness connected to the abdomen 7 of user U, which may define a substantially vertical axis aligned with the spine of the user U for the components carried by or otherwise coupled to the torso brackets 105, 126.

For example, the attachment band 122 may be secured around the user's waist, hips, or other region of the user's torso such that the torso brackets 105, 126 extend from the region to adjacent the user's shoulder. As shown, the torso brackets 105, 126 may extend generally parallel to a substantially vertical axis along the spine of the user U and provide a reference frame relative to which other components of the system 10 may move. Alternatively, the torso brackets 105, 126 may be formed from a single rigid member or separate members joined together, e.g., with a coupling portion (not shown) extending along the attachment band 122 between the lower ends of the brackets 105, 126.

As shown, the torso brackets 105, 126 provide mounting points for shoulder brackets or bars 106, which connect to the torso brackets 105, 126 at vertical pivot joints 107. The vertical pivot joints 107 define vertical axes Vr, Vl. Bearings, bushings, and/or other friction reduction features (not shown) may be employed in vertical pivot joints 107, e.g., to provide minimal resistance to movement of the user U, as described further elsewhere herein. Shoulder brackets 106 may rotate about the vertical pivot joints 107 as shown by arrows 115, 116, providing the user U with the ability to rotate the shoulder brackets 106 as desired about vertical axes Vr, Vl.

The shoulder brackets 106 connect to arm brackets or bars 108, 124 at horizontal pivot joints 109, 125. The horizontal pivot joints 109, 125 define horizontal axes Hr1, Hl1. The sets of vertical and horizontal axes Vr, Hr1 and Vl, Hl1 may intersect one another or may be offset but still generally orthogonal to one another. Bearings, bushings, and/or other friction reduction features (not shown) may also be employed in the horizontal pivot joints 109, 125, as desired. The arm brackets 108, 124 may rotate about the horizontal axes Hr1, Hr2, as shown by arrows 114, 117. The arm brackets 108, 124 carry arm rests or pads 120 or other features at their free ends for supporting the upper arm 5a of the user U while the forearm 5b of the user U remains unsupported, as best seen in FIG. 4A. As shown in FIGS. 2A and 2B, the upper arms 5a of the user U rest in the arm pads 120, which may have a concave shape to enhance support of the upper arm 5a. Optionally, the arm pads 120 may include cushioning elements, e.g., foam, fabric, or other material to provide additional comfort to the user U. In addition or alternatively, if desired straps or other features (not shown) may be provided on the arm brackets 108, 124 and/or arm pads 120 that may be wrapped around the arms 5 or otherwise used to secure the arms 5 relative to the arm pads 120.

Torque elements 112 are connected to the shoulder brackets 106 and arm brackets 108, 124, e.g., at the horizontal pivot joints 109, 125, and apply torsional loads 118, 119 to the arm brackets 108, 124, as indicated by the directions of arrows 118, 119. The torsional loads 118, 119 may act to counterbalance all, or a portion of, the force of gravity Wl, Wr on the arms 5 of the user U. In the embodiment shown, each torque element 112 is a spring mechanism, which provides the exclusive energy source for applying an offsetting force (represented by arrows 118, 119) to the arm brackets 108, 124, as described elsewhere herein.

Figure 3A:
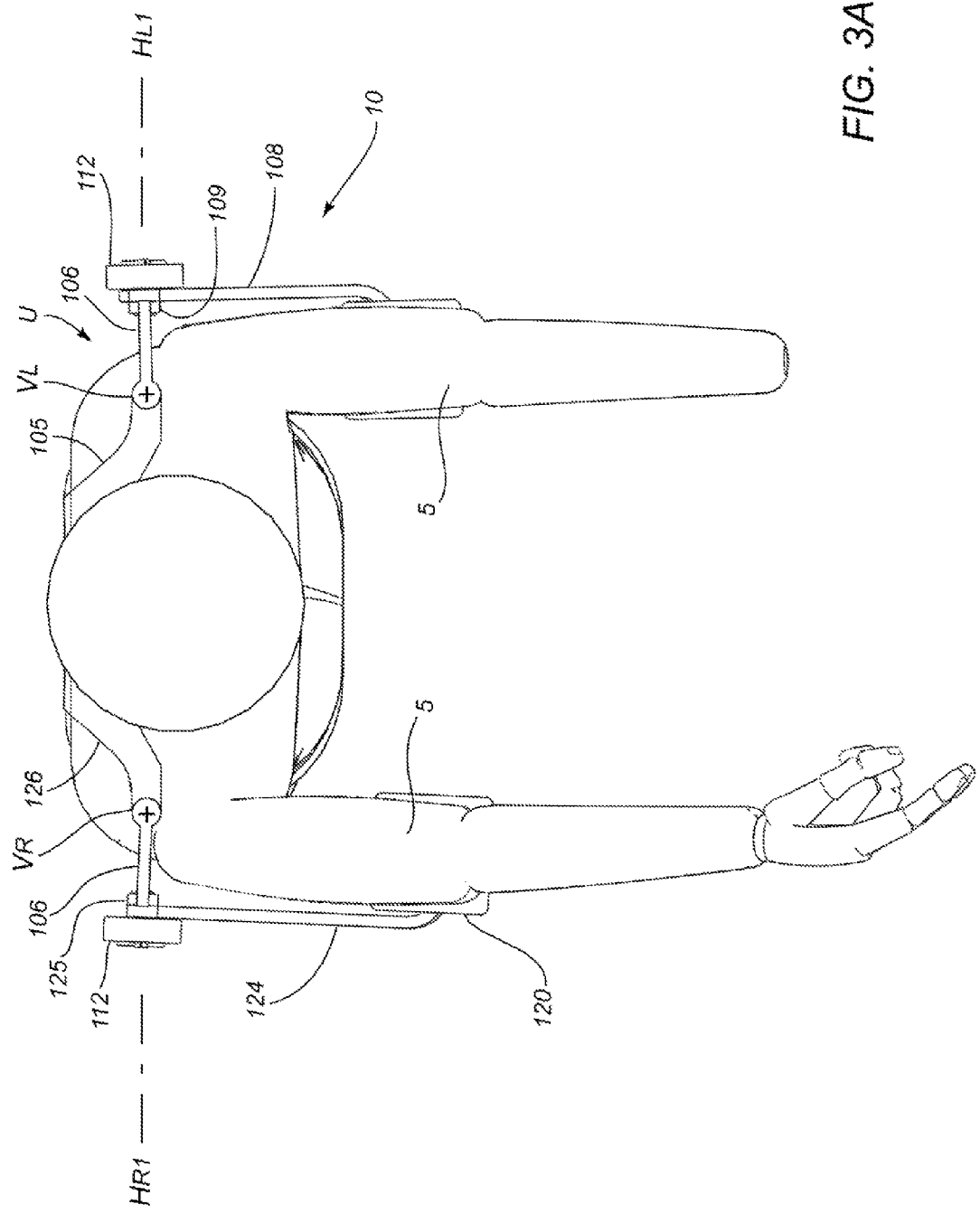

The vertical pivot joints 107 permit shoulder brackets 106 to rotate about vertical axes Vl, Vr. As shown in FIG. 3A, the shoulder brackets 106 generally define horizontal axes Hl1, Hr1. The User U may rotate the shoulder brackets 106 to any desired position consistent with the needs of the task being performed. For example, as shown in FIG. 3B, the user U has moved arm 5 laterally or horizontally, resulting in rotation 130 of the shoulder bracket 106, and defining a new horizontal axis Hr2. Thus, there may be infinite positions of the horizontal axes, as determined by the motion of the arm(s) 5 of the user U.

The horizontal pivot joints 109, 125 also permit infinite positions of the arms 5 of the user U. For example, FIG. 4A shows the user's arm 5 in an essentially horizontal attitude. The force of gravity Wr acts to pull the user's arm 5 downward. Torsional load 118, applied about horizontal axis Hr1 by the torque element 112, acts to counterbalance all or a portion of the gravitational force Wr, and reduce the muscular effort the user U needs to employ to hold the arm 5 outstretched.

FIG. 4B shows the user's arm 5 raised above horizontal along path 134. The torsional load 118 continues to act to at least partially counterbalance gravitational force Wr. FIG. 4C shows the user's arm 5 lowered below the horizontal along path 136. The torsional load 118 may continue to act to at least partially counterbalance gravitational force Wr. Thus, the user U may be able to move their arms 5 to desired positions, while the adaptive arm support system 10 moves with (or "adapts to") the arms 5, simultaneously supporting them without substantially interfering with the movement.

FIG. 4D is a detail view taken from FIG. 4C, showing an exemplary embodiment of the torque element 112. As shown, the torque element 112 may include a clock spring located at or near horizontal pivot joint 125. A pivot shaft 155 is rigidly attached to shoulder bracket 106. The arm bracket 124 is free to rotate about the pivot shaft 155. As shown, a first torque element connection feature 158 on the torque element 112 may be captured in pivot shaft connection feature 156, and a second torque element connection feature 160 on torque element 112 may be captured behind arm bracket connection feature 164. Thus, the torque element 112, coupled to the arm bracket 124 and shoulder bracket 106, may be able to impart a counterbalancing torque 118 to the arm bracket 124. Retaining pin 162 holds the torque element 112 in place on the pivot shaft 155. An optional torsional damping element 170 (not shown) may be located in or adjacent to the horizontal pivot joint 125, e.g., to restrict rotational speed. Optionally, a housing or casing (not shown) may be provided around the torque elements 112, e.g., to protect internal components and/or provide a desired appearance or finish for the system 10.

If desired, the torque element(s) 112 may be removable to permit the user U to adjust the torsional load 118. Optionally, a torque adjustment mechanism 175 may be located in or adjacent to the horizontal pivot joint 125, e.g., to permit the user U to adjust the torsional force 118 of the torque element 112, as desired. For example, the user U may prefer a light counterbalancing torque that compensates for approximately 40% of the gravitational forces Wl, Wr that may act on the user's arms 5 (under-compensation). In another example, the user U may prefer a high counterbalancing torque that compensates for approximately 115% of the gravitational forces Wl, Wr on the user's arms 5 (over-compensation).

Figure 5A:
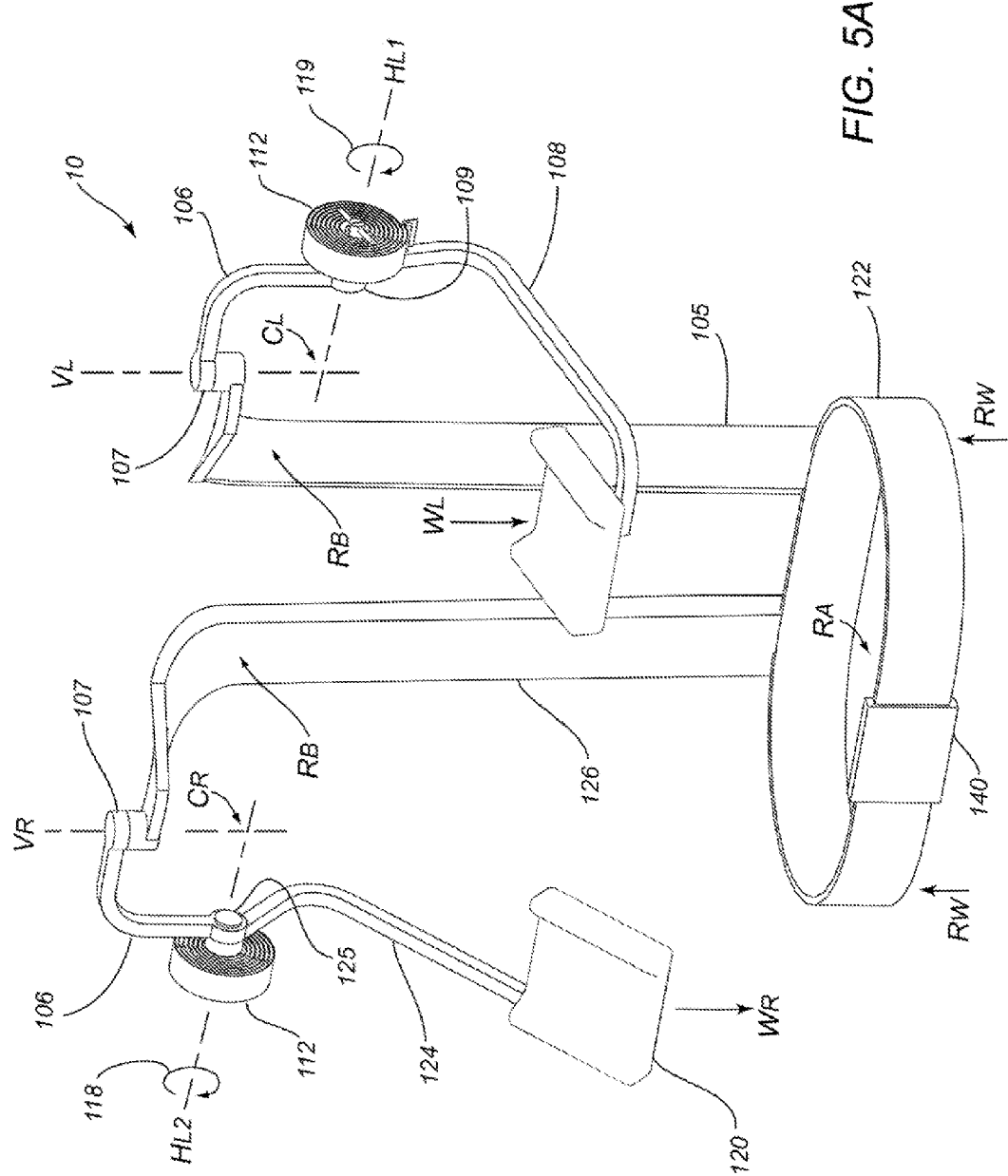
FIGS. 5A and 5B show front and rear perspective views, respectively, of the body-mountable adaptive arm support system of FIGS. 2-4 removed from the user.
Figure 5B:
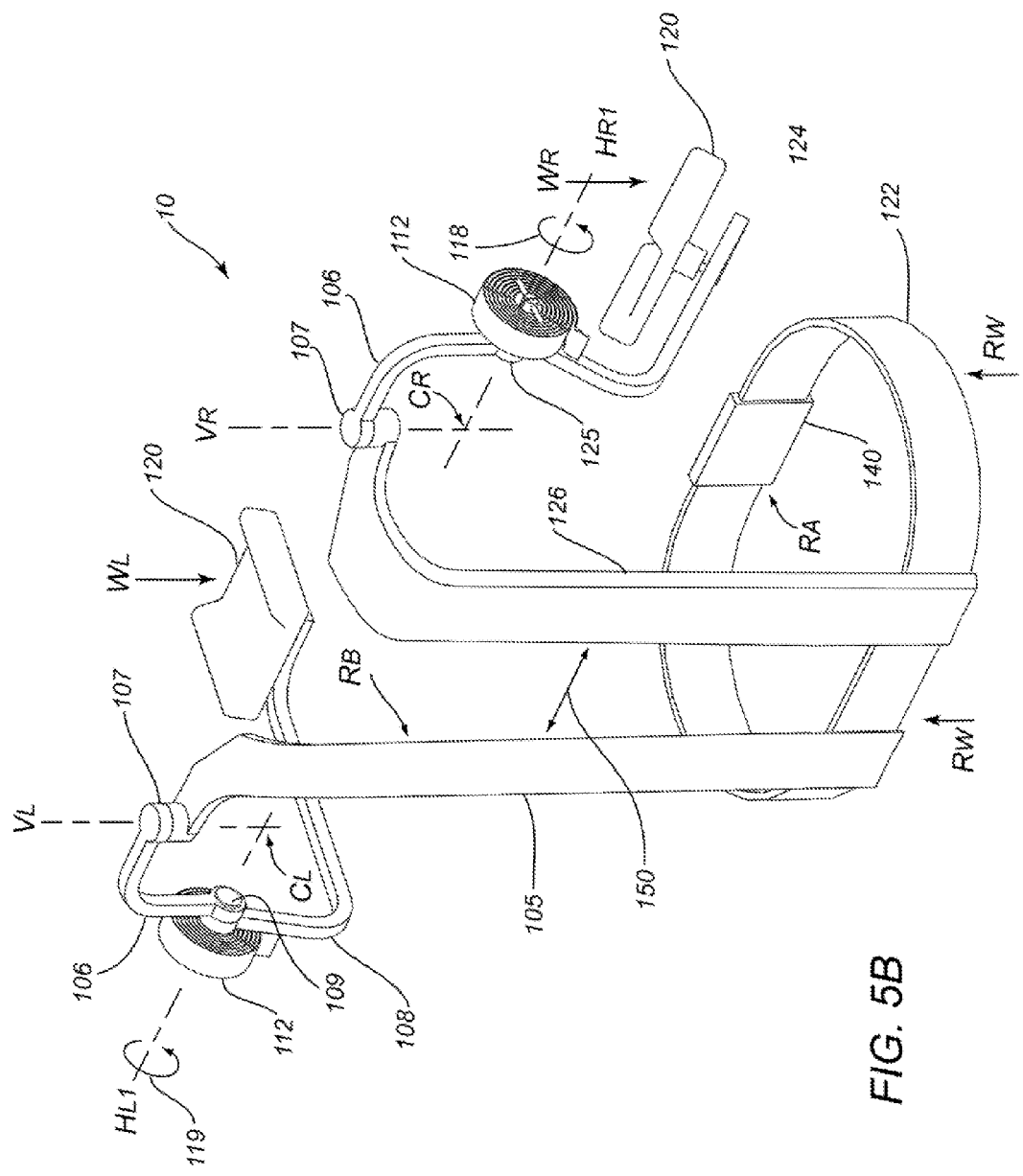

FIGS. 5A and 5B show the adaptive arm support system 10 with the user U omitted merely for clarity. The forces of gravity Wl, Wr on the outstretched arms 5 of the user U may be transmitted through the arm brackets 108, 124, horizontal pivot joints 109, 125, shoulder brackets 106, and vertical pivot joints 107 to the torso brackets 105, 126. The torso brackets 105, 126 are, in turn coupled to one or more attachment bands or other features secured to the user U (one band 122 shown). These three elements make contact with the torso of the user U, e.g., at or around the abdomen 7, and provide a support for transmitting the forces and/or torques input to the adaptive arm support system 10 by the user's arms 5 to other portions of the user's body. Thus, other portions of the body may substantially bear the load of the user's arms 5, rather than the arms 5 themselves.

Preferably, the areas bearing these loads do not require muscular activity to do so. For example, reaction forces Rb, Ra, Rw applied by the user's abdomen 7 by the adaptive arm support system 10 may balance the load of the user's arms 5. Reaction force Rb, for example, may be applied to the adaptive arm support system 10 by a force from a portion of the user's back.

The torso brackets 105, 126 may be rigid, semi-rigid, or flexible, or may have portions of any or all of these. For example, the torso brackets 105 and 126 may have rigid portions joined to semi-rigid portions. In the embodiment shown, each of the torso brackets 105, 126 include a single element that extends substantially parallel to a vertical axis defined by the user's spine from a first end attached to the attachment band 122 to a second end coupled to the vertical pivot joints 107. Alternatively, the torso brackets 105, 126 may include multiple elements attached together. For example, a pair of bracket elements may be adjustably coupled together such that the distance between the first and second ends, i.e., between the attachment band 122 and the vertical pivot joints 107 may be adjusted and fixed, e.g., to accommodate different height users (not shown).

The attachment band 122 may be rigid, semi-rigid, flexible, or may have portions of any or all of these. Optionally, the attachment band 122 may include one or more band adjustment features 140, e.g., to provide a mechanism for adjusting and fixing attachment band 122, e.g., a buckle, hook and eye fasteners, snaps, laces, and the like (not shown), which may facilitate the system 10 being secured around the waist or hips of the user U. The first ends of the torso brackets 105, 126 may be fixed relative to the attachment band 122 or may be adjustable relative to the attachment band 122, for example, laterally along path 150, e.g., using buckles, hook and eye fasteners, and the like (not shown). In addition or alternatively, the location of the first ends of the torso brackets 105, 126 may also be adjustable vertically relative to the attachment band 122, e.g., to accommodate different height users. In a further alternative, multiple systems may be provided, having different dimensions, such that a user may select a system best suited to their body's size and shape.

Figure 6A:
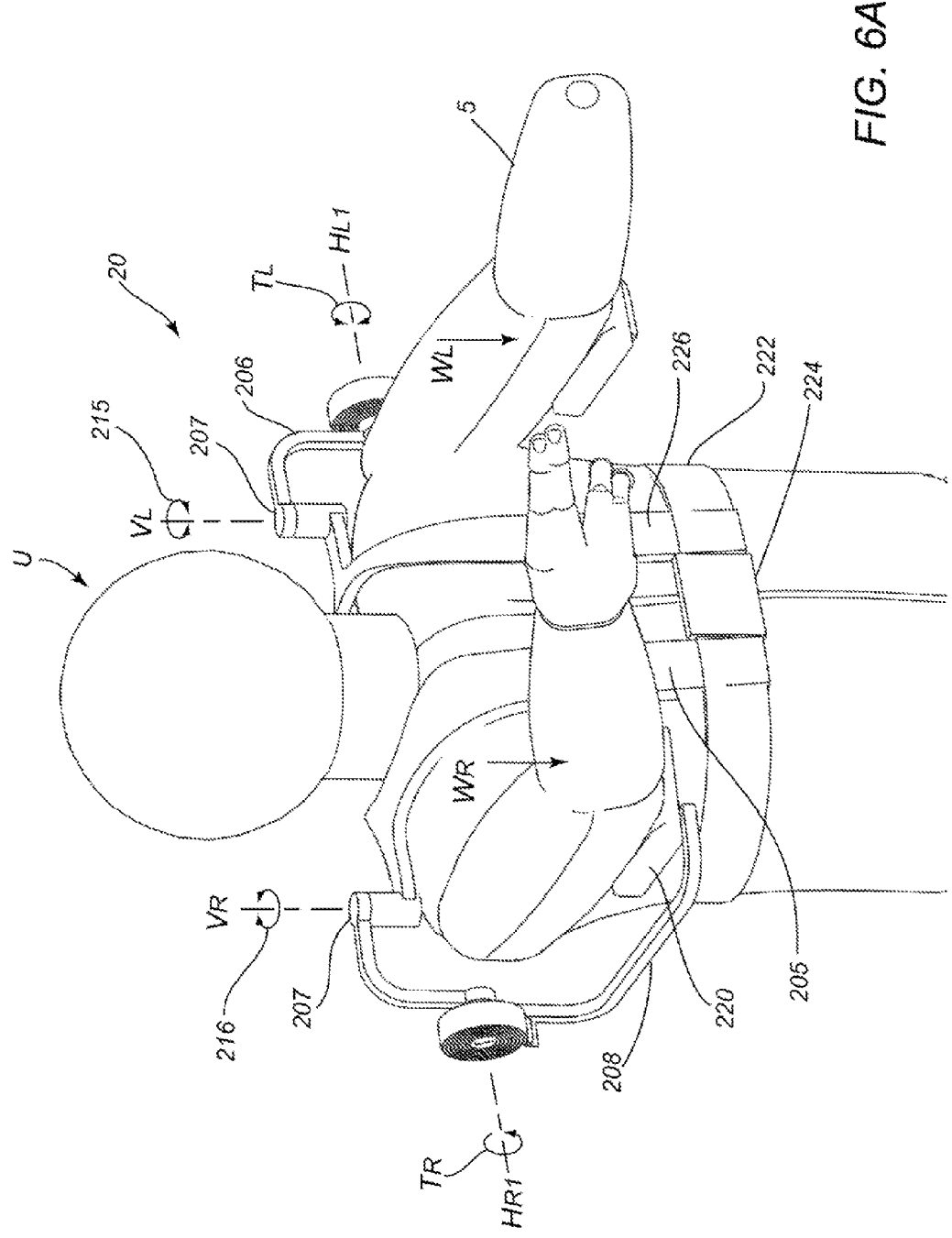
FIGS. 6A and 6B show front and rear perspective views, respectively, of an alternative body-mounted adaptive arm support system.
Figure 6B:
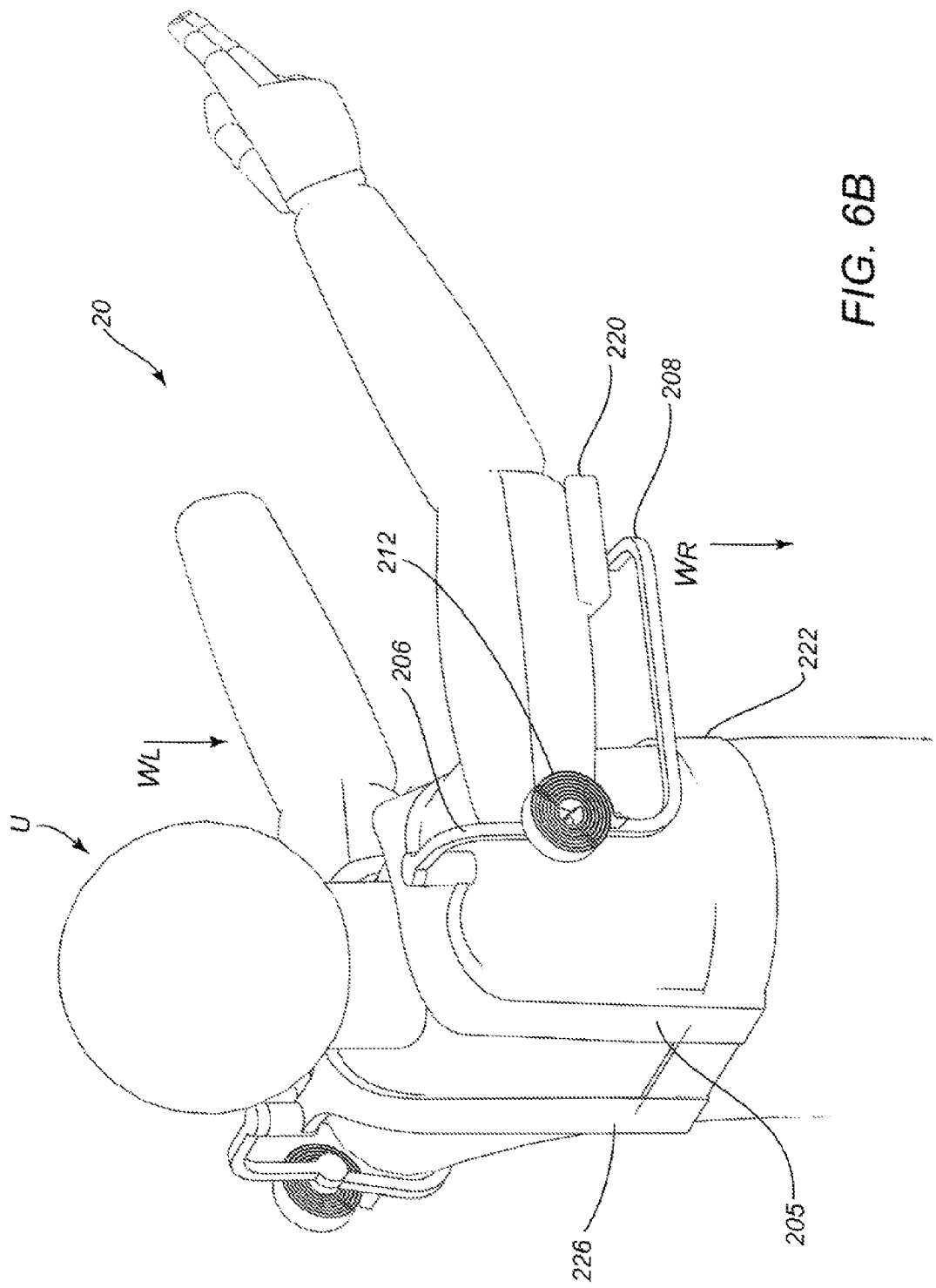
Figure 7A:
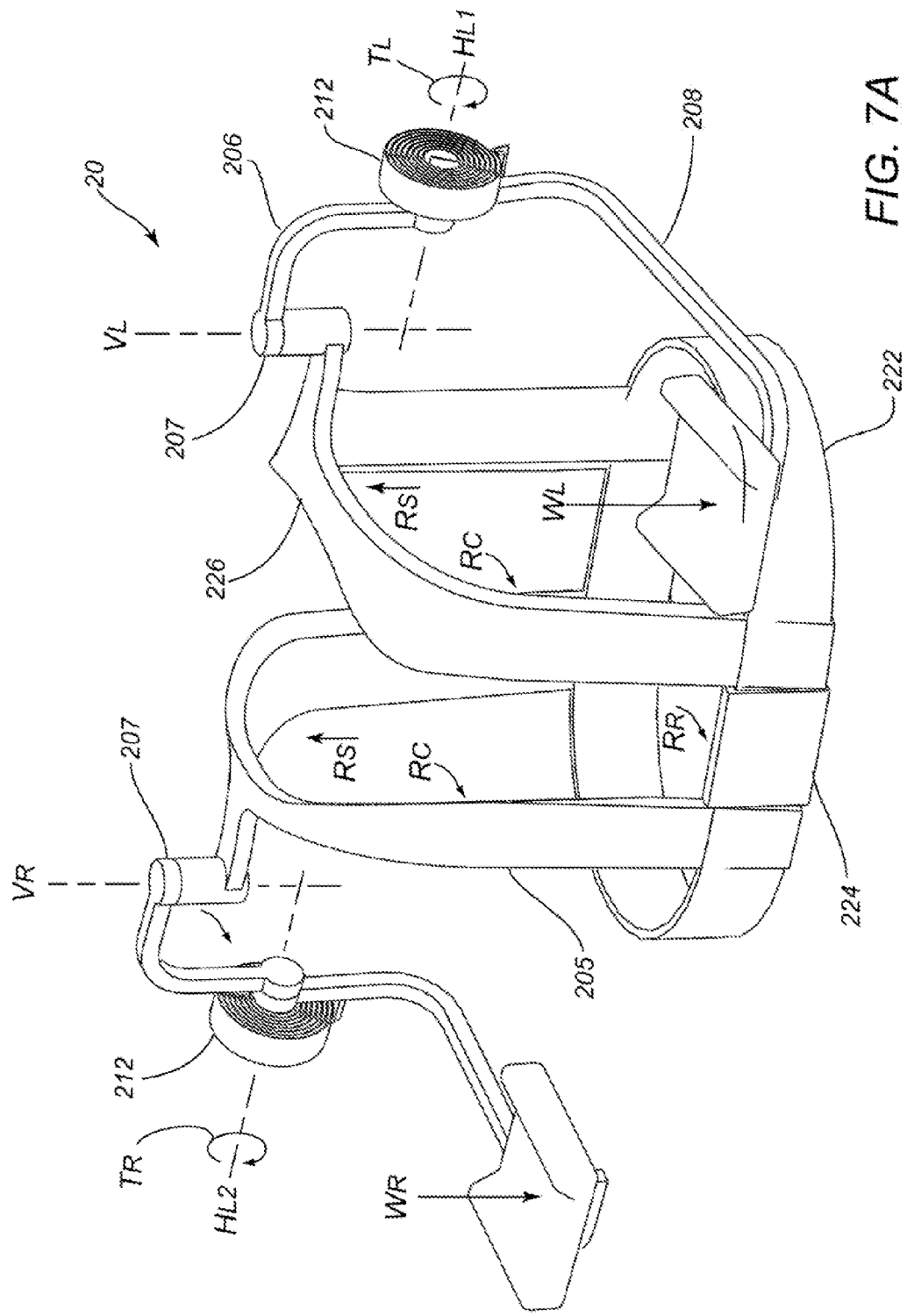

Turning to FIGS. 6A and 7B, an alternative embodiment of an adaptive arm support system 20 is shown that includes many features similar to system 10 (with like features including reference numbers increased by 100). Unlike the adaptive arm support system 10, however, the alternative adaptive arm support system 20 includes torso brackets 205, 226 that are configured to extend over the shoulders of the user U and/or that join the attachment band(s) 222 at multiple points. Optionally, the system 20 may include a band adjustment feature 224, e.g., to provide a mechanism for adjusting and/or securing the attachment band 222 around the torso of the user U. Reaction forces Rc, Rs, Rr (shown in FIGS. 7A and 7B), applied by the user's abdomen 7 on the adaptive arm support system 20, may balance the load Wl, Wr of the user's arms 5.

In alternative embodiments, other mounting features may be provided for securing the adaptive arm support system 10 or 20 to the torso of a user U, in addition to or instead of the torso brackets and attachment bands, for example, harnesses, backpacks, laces, belts, jackets, and/or other garments, and the like (not shown). Such mounting systems may support the system 10 or 20 at one or more locations, e.g., at the shoulders, around the chest, the waist, hips, and/or other regions of the torso, depending on the degrees of freedom of movement desired by the user. For example, a system supported at the shoulders and/or chest may allow the user U to pivot about their waist easier than a system supported at the waist or hips.

Figure 8:
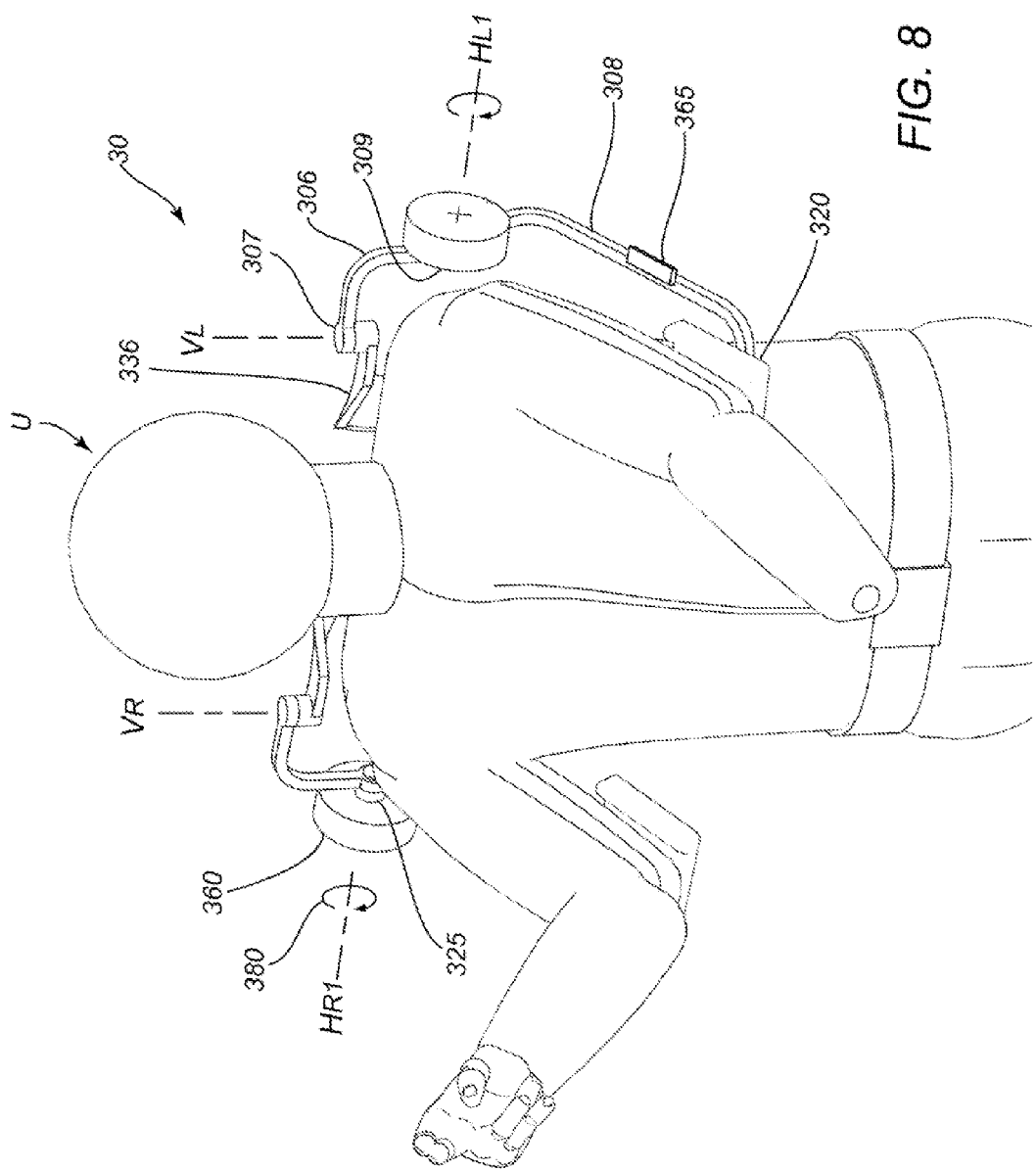
FIG. 8 shows a front perspective view of another embodiment of a body-mountable adaptive arm support system with alternative torque elements.

In further alternative embodiments, other compensation elements may be included in the systems 10 or 20 instead of torque elements 112, 212, if desired. For example, as shown in FIG. 8, a system 30 is shown that is generally similar to the systems 10 or 20, but includes alternative torque elements 360 at horizontal pivot joints 309, 325. In exemplary embodiments, the alternative torque elements 360 may be electric, magnetic, pneumatic, hydraulic, and the like. In addition or alternatively, the alternative torque elements 360 may be battery-powered, self-contained, tethered, attached to external power sources, e.g., by one or more cables (not shown), and the like.

For example, one or more sensors may be provided on the arm support, e.g., sensor 365 shown on arm bracket 308 in FIG. 8, and one or more controllers (not shown) may be coupled to the sensor(s) and to one or more actuators or other compensation elements, in turn, coupled to the arm support. The controller may periodically, intermittently, or substantially continuously acquire data from the sensor(s) to determine the orientation and/or obtain other information regarding the arm support, and activate the actuator(s) or other compensation element(s) based on the data to apply a force to the arm support to at least partially offset the component of gravitational force and/or otherwise transfer a portion of the weight of the user's arm to the harness and/or other region of the user's body.

For example, in the embodiment in FIG. 8, the torsional loads applied by the torque elements 360 may be adjustable, for example, by adjusting current to an electric torque element 360 (or, similarly, fluid pressure to a pneumatic or hydraulic torque element, not shown), e.g., using a controller (not shown) carried on the system or at a nearby location. For example, attitude sensor(s) 365 may be provided, e.g., attached to or otherwise carried by arm brackets 308, that provide position and/or angle feedback to the controller. The controller, in turn, may determine a component of gravitational force acting on the user's arm and activate the torque element 360 (or other actuators or other compensation elements, not shown) to adjust a counterbalancing torsional load 370, 380 generated by the alternative torque elements 360 to suit the user's requirements. For example, the attitude sensor 365 may signal that the user's arm is in a certain position, requiring an increase in the current to an electric torque element 360 to increase the opposing force to enhance support of the arm or, conversely, requiring a decrease in the current to reduce the opposing force if less support is needed.

Optionally, damping may be provided, e.g., by mechanical, pneumatic, hydraulic, electric elements, and the like. For example, mechanical dampers, flow controls, electrical controls, and the like (not shown) may be employed, e.g., to restrict rotational speeds.

In some cases, the user U may want to disable all or a portion of any of the adaptive arm support systems herein, e.g., systems 10, 20, or 30. FIG. 9 shows an adaptive arm support system 10, similar to that shown in FIGS. 1-5, with the right arm support locked in a back or inactive position out of the way of the user's arm 5. Various locking mechanisms (not shown) may be employed, for example, clips, hooks, straps, magnets, threaded fasteners, hook-and-loop fasteners, and the like. Such a lock-out feature may be provided for one or both of the arm supports 108 of the system 10 of FIG. 9 or for the arm support of a system including only a single arm support, such as those described elsewhere herein.

Alternatively, torque elements 360, such as that shown in FIG. 8, may include lock-out features, such as those listed above, which may be activated, e.g., utilizing electric current, pneumatic pressure, hydraulic pressure, and the like, to direct the arm support to a back position away from the user's arm 5 such that the user may move the arm 5 independent of the system 10. In a further alternative, in the absence of electric current, pneumatic pressure, hydraulic pressure, and the like, the user may manually or otherwise control the torque elements 360 to direct the arm support to the back or inactive position.

In some cases, the user U may only want a portion of the adaptive arm support systems described above. For example, FIG. 10 shows an adaptive arm support system 40 that supports only the right arm 5 of the user U. The adaptive arm support system 40 may employ any or all of the features of the other adaptive arm support systems described elsewhere herein, such as systems 10, 20, or 30.

Alternative mounting and load transfer arrangements are contemplated that may be included in any of the embodiments herein, if desired. For example, turning to FIG. 11, a user U is shown wearing an adaptive arm support system 400 that includes a shoulder harness 404, a pair of attachment bands 412, 410, and one or more elongate support elements 408 (two shown). The shoulder harness 404 may include left and right panels 406 formed to fit over or around the user's shoulders, each of which may have a torso bracket 416 mounted thereto. The shoulder harness 404 may be formed from flexible material, such as polymers, leather, composite materials, and the like, or may be formed from rigid, semi-rigid, and/or malleable materials, such as metals, plastics, composite materials, and the like. Similarly, the attachment bands 412, 410 may be formed from flexible or semi-rigid materials, and/or elastic or inelastic materials, similar to other embodiments herein.

As shown in FIG. 11, the torso bracket 416 is coupled to a unitary, L-shaped shoulder bracket 106 at 5 vertical pivot joint 107, e.g., similar to other embodiments herein. A single unitary arm bracket 108 is coupled to the shoulder bracket 106 at horizontal pivot joint 109, and carries an arm pad 120, also similar to other embodiments herein. Optionally, the vertical and/or horizontal pivot joints 107, 109 may be substantially concentric or otherwise aligned with the user's shoulder joint (not shown), which may enhance the arm bracket 108 following movement of the user's arm 5 with 10 minimal interference. One or more torque or other compensation elements 112 may be coupled to the shoulder and arm brackets 106, 108, similar to other embodiments herein, e.g., to provide a torsional load to compensate at least partially for the weight of the user's arm 5.

Also as shown in FIG. 11, a pair of elongate support element(s) 408 are provided as part of the harness, e.g., connected to the shoulder harness 404 at a first or upper end 414, and to the optional waist strap or attachment band 412 at a second or lower end 418. In addition or alternatively, the optional chest strap or attachment band 410 may be provided, e.g., to enhance securing the left and right forms 406 of the shoulder harness 404 to the user U. Optionally, the elongate support element(s) 408 may include springs, rods, cables, and/or other components, which may be formed from elastomeric or polymeric, solid, hollow, pressurized, rigid, semi-rigid, and/or flexible materials. The support element(s) 408 may enhance transmitting the weight of the user's Arm 5 to the waist strap 412, thus distributing the weight over the waist and hips of the user.

The support element(s) 408 may be substantially straight as shown, or may be curved, angled, or twisted, as desired to provide desired support with minimal discomfort or inconvenience to the user wearing the system 400. In addition or alternatively, the support elements 408 may include one or more telescoping or pivoting elements (not shown). The top and/or bottom junctions 414, 418 may be rigid or may include pivoting joints, similar to other embodiments herein.

Turning to FIGS. 12A and 12B, still another alternate adaptive arm support system 420 is shown that is generally similar to the system 400 shown in FIG. 11. However, the adaptive arm support system includes a pair of support elements 422 that are attached to a shoulder harness 415 and a waist attachment band 417 by upper and lower pivoting junctions 424, 426, which may pivot about axes 430, 431. In addition or alternatively, the support elements 422 may also pivot about longitudinal axes 436, 441. For example, as shown in FIG. 12B, motion of the user U bending forward to achieve a task may result in rotation or pivoting of the support elements 422, e.g., to accommodate the user's motion approximately along path 440. Alternatively, the pivoting junctions 424, 426 may pivot about axes 430, 431, and the support elements 422 may pivot about the longitudinal axes 436, 441, e.g., to allow the support elements 422 to bend freely. During such movement, the support elements 422 may continue to transmit at least a portion of the weight of the user's Arm 5 to the waist support band 417, although by bending along path 440, the support elements 422 may accommodate bending motion of the User U. Alternatively, the support elements 422 may be fixedly coupled to one or both of the shoulder harness 415 and the attachment band 417. Optionally, the support element(s) 422 may include one or more of springs, rods, cables, and the like, may be formed from elastomeric or polymeric, solid, hollow, pressurized, rigid, semi-rigid, and/or flexible materials, similar to other embodiments herein.

Figure 13:
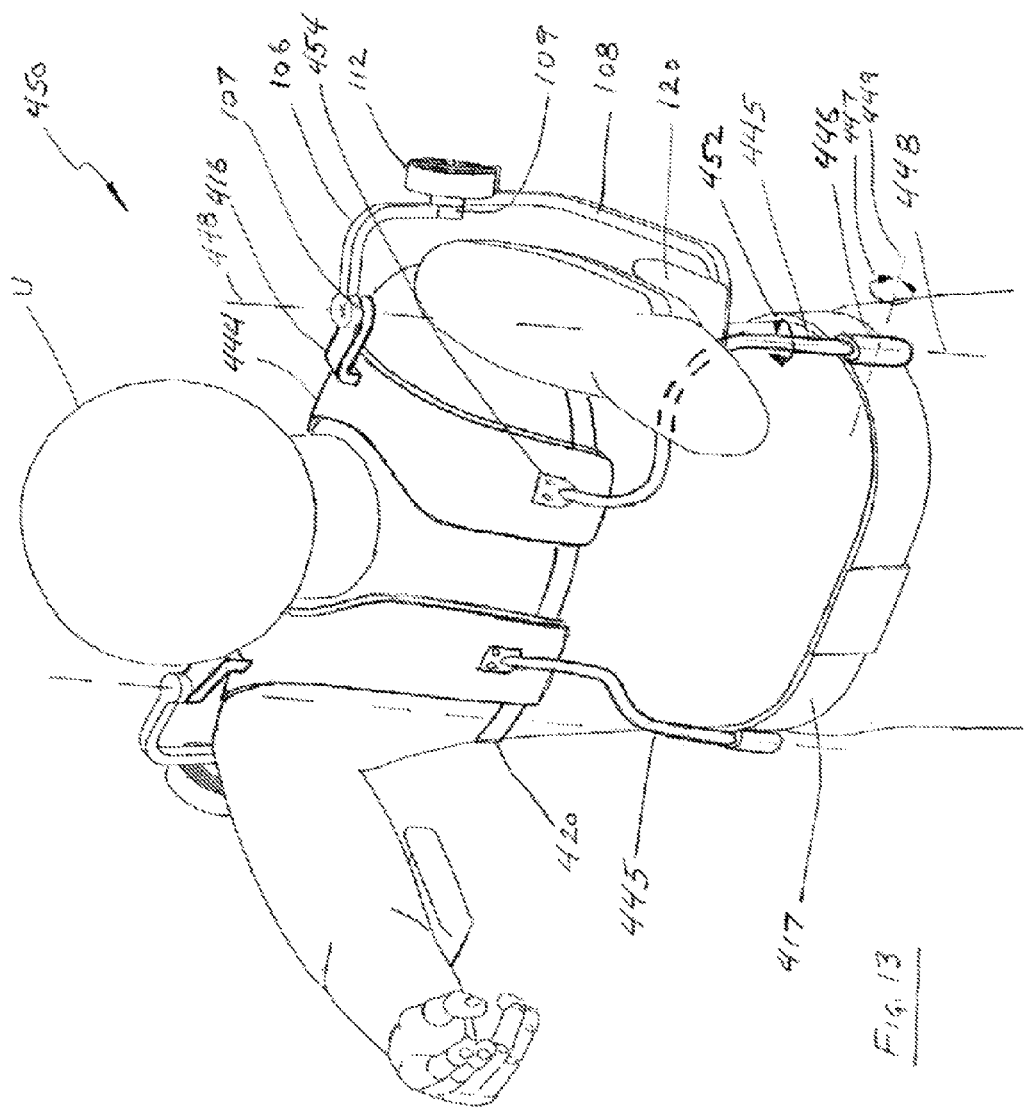

In other embodiments, it may be advantageous to have elements of the adaptive arm support systems herein positioned at different positions and/or angles relative to the user's shoulder. For example, in FIG. 13, an adaptive arm support system 450 is shown that is generally similar to other embodiments herein. The system 450 includes one or more support element 445 (two shown) joined to a shoulder harness 444 at joint 454 and joined to a waist support strap 417 at axis mount 446. A longitudinal axis 448 may be substantially concentric and/or aligned with the axis mount 446 and the user's shoulder joint. In addition or alternatively, the support element(s) 445 may optionally pivot within the axis mount 446, e.g., approximately along path 452.

The axis mount 446 may be mounted at any location around the periphery of the waist support strap 417 and/or may be appropriately angled relative to the vertical axis of the system 450. For example, the axis mount 446 itself may optionally pivot about pivot axis 449, e.g., approximately along path 447. The support element(s) 445 may be constructed similar to other embodiments herein, e.g., including springs, rods, cables, and the like, formed from elastomeric or polymeric, solid, hollow, pressurized, rigid, semi-rigid, and/or flexible materials.

In other embodiments, it may be advantageous to have elements of the adaptive arm support systems not concentric or aligned relative to the user's shoulder. For example, in FIG. 14, an adaptive arm support system 460 is shown that includes support element(s) 458 coupled to a shoulder harness 456 at joint 464 and to a waist support strap 417 at axis mount 462. Similar to other embodiments herein, the axis mount 462 may be mounted at any location on the waist support strap 417, and/or may be appropriately angled. For example, the axis mount 462 may define a longitudinal axis 468 that is non-concentric or off-axis with user's shoulder joint, e.g., such that the axes may intersect or otherwise extend non-parallel to one another. Optionally, the support element(s) 445 may pivot within the axis mount 446, e.g., approximately along path 468. The support element(s) 458 may be springs, rods, cables, and the like, formed from elastomeric or polymeric, solid, hollow, pressurized, rigid, semi-rigid, and/or flexible materials, similar to other embodiments herein.

Turning to FIGS. 15A and 15B, another embodiment of an adaptive arm support system 480 is shown that is generally similar to other embodiments herein, although the system 480 includes only one arm support. As shown, the adaptive arm support system 480 includes a torso bracket 486 mounted on a shoulder harness 484, a shoulder bracket 492 pivotally coupled to the torso bracket 486, and an arm bracket 502 pivotally coupled to the shoulder bracket 492, e.g., generally similar to other embodiments herein. Unless the previous embodiments, the system 480 includes an adjustment mechanism for adjusting a torque element 500 thereon. The torque element 500 may be mounted substantially concentrically with and/or otherwise coupled to a shaft 517, e.g., to at least partially compensate for the gravitational force acting on the arm support 502, similar to other embodiments herein.

In the embodiment shown, the adjustment mechanism includes a torque adjustment knob 514 coupled to a worm screw 516, which is, in turn, coupled to a work gear 518 coupled to the shaft 517. When the torque adjustment knob 514 is rotated, the worm screw 516 rotates the worm gear 518, which consequently rotates the shaft 517 to increases or decreases the torque provided by the torque element 500, thereby modifying the compensation for the user's Arm 5. It will be appreciated that such an adjustment mechanism may be provided on any of the embodiments described elsewhere herein.

Turning to FIGS. 16A-16H, an adaptive arm support system 480 is shown, similar to that shown in FIGS. 15A and 15B, that includes a locking mechanism to "lock" the arm bracket 502 and/or other components of the arm support out of the way when the arm bracket 502 is not needed, and/or a safety "brake" to prevent the arm support from moving unexpectedly, which may also be provided on any of the other embodiments herein. FIGS. 16A through 16H illustrate these features (where, for clarity, the torque element 500 shown in FIGS. 15A and 15B has been omitted to show features of the locking mechanism). As shown in FIG. 16A, the adaptive arm support system 480 includes an arm bracket 502 that is coupled at a first end to a pivot block 528 and that carries an arm pad 508 on its second, free end, similar to other embodiments herein. The pivot block 528 may pivot freely about shaft 517. A safety bar 504 also pivots about the shaft 517.

A spring or other biasing mechanism 526 applies a desired separation force between the arm bracket 502 and safety bar 504. However, pressure from the user's arm 5 on the safety bar 504 may compress the spring 526, and hold the safety bar 504 generally parallel to the arm bracket 502. In this "active" position, the adaptive arm support system 480 is active and at least partially compensating for the weight of user's Arm 5.

In the active position, a safety pawl 546 (attached to the pivot block 528) is in its normal position, with a tip 550 of the safety pawl 546 disengaged from safety plate teeth 536 on a safety plate 534 mounted on the shoulder bracket 492. In this position, the user U may move the arm 5 as desired, with a compensation force being provided by the torque element 500 (not shown, see FIGS. 15A and 15B). Consequently, similar to other embodiments herein, the arm bracket 502 may rotate about the shaft 517 relative to the shoulder bracket 492, and "follow" movement of the arm 5.

If it is desired to disengage the adaptive arm support 480, the user U pushes the arm bracket 502 back into a "lock out" or "inactive"position generally along path 560, as shown in FIGS. 16B and 16C (which shows a back view of the adaptive arm support system 480). The user U may then rotate the arm bracket 502 generally along path 574, as shown in FIG. 16D, which causes the arm bracket 502 to "hook" on or otherwise engage a lock-out pin 566 mounted on a hub block 529 on the shoulder bracket 492. Once the arm bracket 502 is "hooked" out of the way on lock-out pin 566, the user U may disengage the arm 5, leaving the arm bracket 502 "locked" out of position. FIG. 16E shows a back view of the user U moving the arm 5 away from locked-out arm bracket 502, while FIG. 16F shows this motion from the side.

As the user U moves the arm 5 generally along the path 582, the arm bracket 502 is restrained by the lock-out pin 566, and consequently remains substantially stationary. The safety bar 504 is then urged away from the arm bracket 502 generally along the path 588 under the influence of the spring 526. As the safety bar 504 separates from the arm bracket 502, a cam feature 540 on the safety bar 504 engages the safety pawl 546 and pushes the safety pawl 546 outwardly generally along the path 586. As the safety pawl 546 is pushed outwardly, the safety pawl tip 550 engages the safety plate teeth 536 on the safety plate 534, preventing rotation of the arm bracket 502. Once the user U has "locked" the arm bracket 502 back, the user U may use the arm 5 independently, i.e., without the adaptive arm support 480 following the movement and/or compensating for the arm's weight (as shown in FIGS. 16G and 16H).

When the user U wishes to re-engage the adaptive arm support system 480, the user U may perform the steps shown in FIGS. 16A through 16H in reverse order, e.g., to reengage the safety bar 502, release the safety pawl 546, and disengage the lock-out pin 566, thereby allowing the arm bracket 502 to subsequently support the arm 5.

If the user U accidentally separates the arm 5 from the adaptive arm support system 480 of FIGS. 15A-15B and/or FIGS. 16A-16H, the system 480 may include safety "brake" features to prevent unwanted and/or uncontrolled motion. For example, turning to FIG. 17A, the user U is shown using the adaptive arm support system 480 normally. If the user's arm 5 slips out of the arm pad 508, as shown in FIG. 17B, the torque element 500 may try to urge the arm bracket 502 generally along path 600 in an uncontrolled motion. The absence of the user's Arm 5 on the safety bar tab 506 of the safety bar 504 permits the safety bar 504 to separate from the arm bracket 502 under the influence of the spring 526, generally along path 602.

As shown in FIG. 16C, however, separation of the safety bar 504 from the arm bracket 502 causes the cam feature 540 on the safety bar 504 to engage the safety pawl 546 and push the safety pawl 546 outwardly generally along path 604. As the safety pawl 546 is pushed outwardly, the safety pawl tip 550 may engage the safety plate teeth 536 on the safety plate 534, as shown in FIG. 17C, thereby preventing unwanted and/or uncontrolled rotation of the arm bracket 502. It will be appreciated that other safety elements may be included in the systems herein for preventing unwanted and/or uncontrolled motion of the arm support(s), e.g., based on rotational velocity, including centrifugal clutches, hydraulic dampers, spring-wrap clutches, and the like (not shown).

Optionally, any of the embodiments herein may include one or more features to ease reaching overhead. For example, turning to FIGS. 18A and 18B, another embodiment of an adaptive arm support system 590 is shown that includes a shoulder bracket 492 and arm bracket 502, generally similar to other embodiments. Unlike the previous embodiments, the system 590 includes an additional pivot joint 596, anchored on a stanchion 594, which is mounted or otherwise secured to a shoulder harness 484. In addition, in this embodiment, an extension bracket 592 is attached to a torso bracket 486 and is pivotally coupled to the stanchion 594 at the pivot joint 596. The torso bracket 486 may contact a stop feature 597 on the shoulder harness 484, preventing clockwise rotation (from the perspective of FIG. 18A). Thus, when the user's arm 5 is moved horizontally or below horizontal, the system 590 may operate similar to other embodiments herein.

However, when the user U reaches overhead, as shown in FIG. 18B, the extension bracket 592, coupled to the torso bracket 486 and other brackets of the system 590, may pivot generally along path 598, thereby avoiding interference between the user's shoulder and the adaptive arm support system 590. It will be appreciated that such a configuration may be provided on any of the embodiments described elsewhere herein.

It will be appreciated that other compensation elements may be included in any of the embodiments herein, e.g., instead of the torque elements 112, 212, 500 described previously, to provide a compensation force to at least partially compensate for the weight of a user's arm 5. For example, turning to FIGS. 19A and 19B, another embodiment of an adaptive arm support system 610 is shown that includes a torso brackets 612, 614 or other harness (not shown), a shoulder bracket 618 pivotally coupled to the torso bracket 614, and an arm bracket 624 pivotally coupled to the shoulder bracket 618, similar to other embodiments herein. In addition, unlike the previous embodiments, the system 610 includes a biasing mechanism, e.g., an extension spring 632 that may be coupled to or otherwise interact with a set of gears to provide a compensating force.

As shown, the shoulder bracket 618 includes an extension bracket 638 attached or otherwise fixed thereto, and a sector gear 620 pivotally coupled thereto by pivot joint 630. Each of the extension bracket 638 and the sector gear 620 include a pin or other connector 636, 634, respectively. The extension spring 632 is coupled between the extension bracket 638 and the sector gear 620, at the pins 636, 634. The sector gear 620 includes a plurality of teeth 621, which mesh with corresponding teeth 630 on an arm bracket gear 628 attached to the arm bracket 624. As shown in FIG. 19A, as the user U raises the arm 5, the arm bracket 624 follows the movement under the influence of the extension spring 632, generally along path 644, providing a compensating force. Simultaneously, the sector gear 620 pivots about the pivot joint 622 generally along path 642. Conversely, as shown in FIG. 19B, when the user U lowers the arm 5, the arm bracket 624 follows generally along path 646, as the sector gear 620 pivots about the pivot joint 622, generally along path 648. Although an extension spring 632 is shown, it will be appreciated that other biasing mechanisms may be provided instead, such as an air spring, a polymer strap, an elastomer strap, and the like (not shown).

Figure 20A:
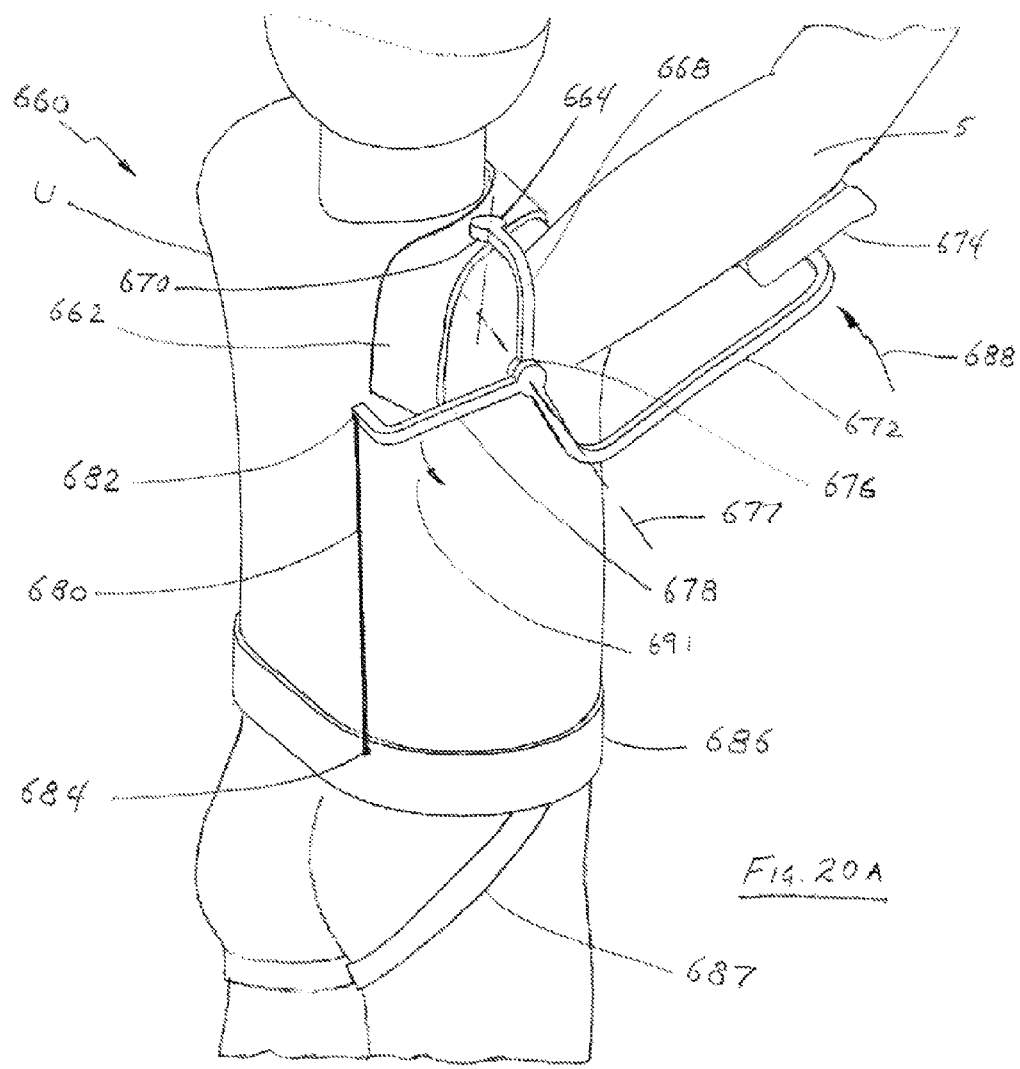
Figure 20B:
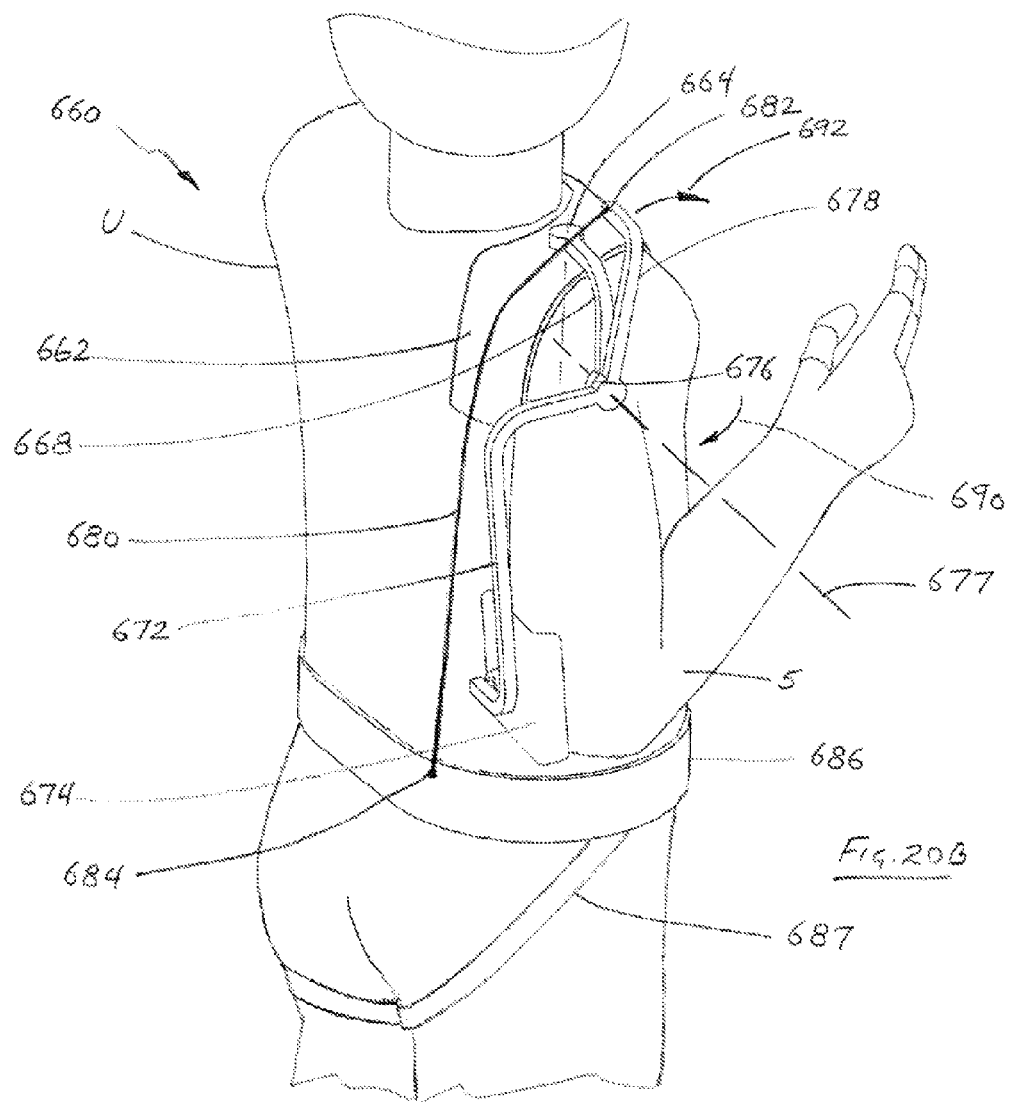

Turning to FIGS. 20A and 20B, still another embodiment of an adaptive arm support system 660 is shown that includes a compensation element. In this embodiment, the system 660 includes a tension element 680 coupled between a belt or other harness 686 of the system 660 and an arm support, e.g., including an arm bracket 672 and arm pad 674 generally similar to other embodiments herein. As shown, the tension element 680 include a first end attached or otherwise coupled to a belt 686, e.g., at junction 684. Optional straps 687 are shown that are attached to or otherwise extend from the belt 686, e.g., further secure the belt 686 to the user U (which may also be included in any of the other embodiments herein, if desired).

The tension element 680 also includes a second end attached or otherwise coupled to an extension bracket 678 on the arm bracket 672, e.g., at junction 682. During use, as the user U raises the arm 5, as shown in FIG. 20A, the arm bracket 672 may follow the movement under the influence of the tension element 680, generally along path 688, thereby providing a compensating force. As the user U lowers the arm 5, as shown in FIG. 20B, the arm bracket 672 may follow generally along path 690, with the tension element 680 providing a compensating force. In exemplary embodiments, the tension element 680 may be an extension spring, an elastomer spring, a cable, a strap, a cord, and the like.

Turning to FIGS. 21A and 21B, yet another embodiment of an adaptive arm support system 700 is shown that includes a compensation rod 704 as a compensation element to provide a compensating force to a user's arm 5. As shown, a first end of the compensation rod 704 is attached to or otherwise coupled to an attachment band or other harness, e.g., to the front of an abdomen mount 710 at junction 712. A second end of the compensation rod 704 is coupled to and/or carries an arm pad 706, e.g., via an optional spherical or other pivotal joint 708. Optionally, the compensation rod 704 may contact or engage the torso of the user U at other locations, including the shoulder, chest, side, and/or back.

Figure 22A:
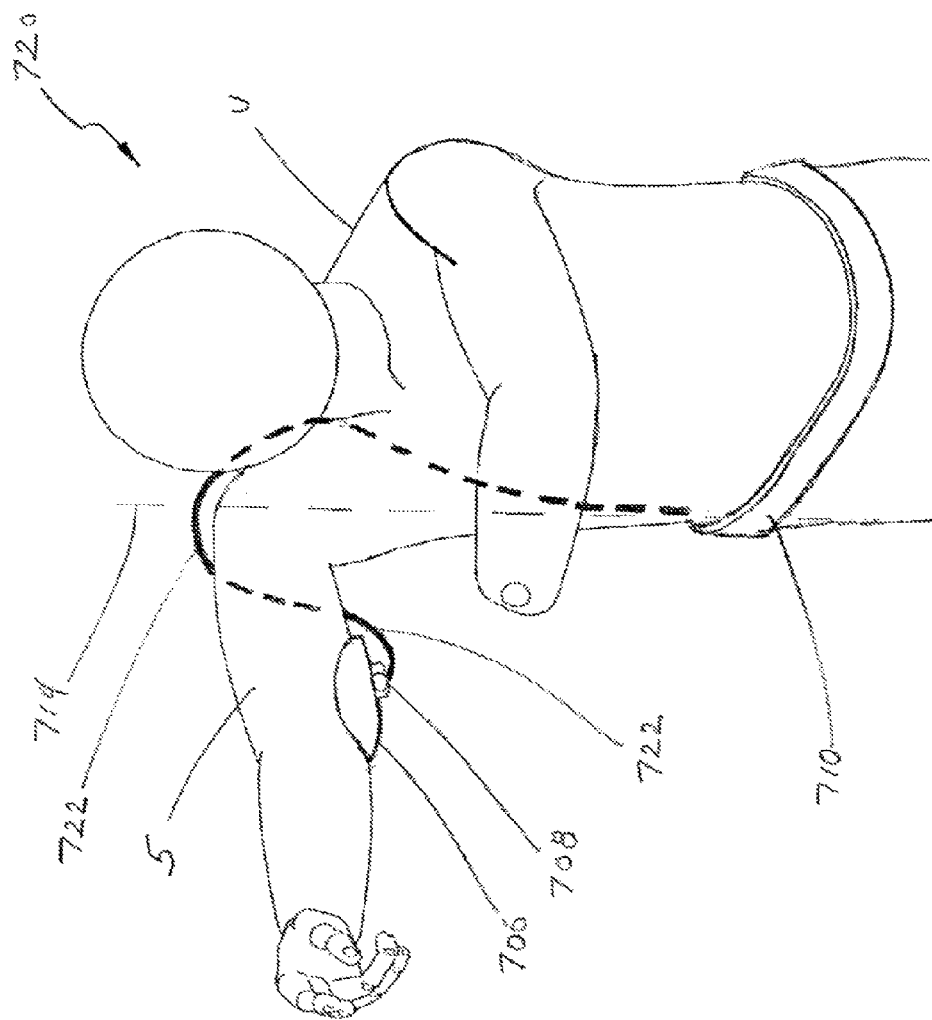

Alternatively, as shown in FIGS. 22A and 22B, an adaptive arm support system 720 may be provided that includes a compensation rod 722 attached to the back or side of an abdomen mount 710 or other harness, e.g., at junction 724. Similar to the compensation rod 704, the compensation rod 722 may be coupled to or carry an arm pad 706, e.g., via an optional spherical or other pivotal joint 708. The compensation rod 722 may support the user's arm 5, providing a compensating force, and/or may optionally contact the user's torso at other locations, including the shoulder, chest, side, and back.

The compensation rods 604, 704 may be formed from flexible or semi-rigid materials that may be biased to a predetermined shape or configuration and/or may otherwise provide a compensating force to at least partially compensate for the gravitational force acting on the users arm 5 as the user U performs one or more tasks, similar to other embodiments.

It will be appreciated that the systems described above may be used in a variety of fields and applications. For example, the systems may be worn by physicians, e.g., surgeons, dentists, and the like, to facilitate extension of the physician's arm(s) during an extended surgical, medical, or dental procedure. The systems may be worn by construction workers, e.g., painters, carpenters, and the like, manufacturing workers, e.g., involved in product assembly, and the like, disabled individuals, and/or other users who perform tasks for an extended period of time in which one or both arms may be extended outwardly from the user's body.

Generally, the systems herein may be worn or otherwise placed on the user's body, e.g., by securing a harness onto the user's torso, e.g., their waist, hips, shoulders, back, chest, and the like. An arm support of the system, e.g., coupled to or otherwise carried by the harness, may be used to support the user's arm such that the arm support subsequently follows movement of the user's arm. The user may then perform one or more tasks involving movement of the user's arm, the arm support at least partially offsetting a gravitational force acting on the user's arm and/or at least partially transferring the gravitational force to the user's torso during the movement without substantially interfering in the movement. Thus, the systems may facilitate the user performing the task(s) for greater lengths of time and/or with reduced fatigue and/or injury.

It will be appreciated that elements or components shown with any embodiment herein are merely exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A support system, consisting essentially of: a harness configured to be worn on a body of a user comprising an attachment band configured to be worn around the torso of the user, a shoulder harness configured to be worn over or around one or both shoulders of the user, and one or more rigid support members extending between the shoulder harness and the attachment band; a bracket comprising a first end mounted to the harness such that a second end thereof is substantially fixed relative to the harness and terminates above the user's shoulder adjacent the arm being supported; an arm support pivotally coupled to the harness comprising a unitary L-shaped first arm support bar pivotally coupled to the second end of the bracket at a first pivot point such that the first arm support bar is rotatable horizontally about a vertical axis relative to the harness, and a single unitary second arm support bar including a first end segment pivotally coupled to the first arm support bar such that a second free end of the second arm support bar is rotatable about a second axis generally orthogonal to the vertical axis, the second arm support bar sized such that the arm support terminates adjacent the user's upper arm and the user's forearm remains unsupported; an arm rest carried by the second arm support bar such that the arm rest rotates about the second axis when the user raises and lowers the upper arm; and a compensation element consisting essentially of a spring mechanism coupled to the first and second arm support bars to at least partially offset a gravitational force acting on the arm support.

2. The system of claim 1, wherein the one or more support members comprise a first support member located on the harness such that the first support member extends along the user's back when the harness is worn on the body of the user, and wherein the arm support is pivotally coupled to the first support member.

3. The system of claim 1, wherein the one or more support members comprise a first set of support members located on the harness such that the first set of support members extend along the user's back when the harness is worn on the body of the user, and a second set of support members located on the harness such that the second set of support members extend along the user's front when the harness is worn on the body of the user.

4. The system of claim 3, wherein the first set of support members are located generally opposite the second set of support members.

5. The system of claim 1, wherein the spring mechanism is configured to apply a variable offsetting force acting on the arm support.

6. The system of claim 1, wherein the entire arm support is sized to terminate at a location above the user's elbow.

7. A system for supporting an arm of a user, comprising: a harness configured to be worn on a body of a user and comprising a shoulder harness configured to be worn over or around one or both shoulders of the user, and one or more support
members defining a vertical axis extending generally parallel to a spine of the user when the harness is worn;
a bracket comprising a first end mounted to the harness such that a second end thereof is substantially fixed and terminates above the user's shoulder adjacent the arm being supported;
an arm support comprising a unitary L-shaped shoulder bracket pivotally coupled to the second end of the bracket such that the shoulder bracket is configured to pivot about a vertical axis at a first pivot point fixed at the second end of the bracket, a single, unitary arm bar including a first end pivotally coupled to the shoulder bracket such that the arm bar is rotatable about a horizontal axis at a second pivot point generally orthogonal to the vertical axis, and an arm rest mounted on the arm bar such that the arm rest rotates about the horizontal axis with the arm bar when the user raises and lowers the upper arm for supporting the user's upper arm, the arm bar sized to extend along the user's upper arm and terminate above the user's elbow such that the user's forearm remains unsupported; and
a spring element coupled to the arm bar and the shoulder bracket, the spring element being the exclusive energy source applying an offsetting force to the arm bar to at least partially offset a gravitational force acting on the arm as the user moves and the arm support follows the movement of the user's arm.

8. The system of claim 7, wherein the harness comprises an attachment band configured to be worn around the torso of the user and one or more rigid support members extending between the shoulder harness and the attachment band.

9. The system of claim 8, wherein the attachment band is configured to be secured around one of a waist, hips, or chest of the user.

10. A system for supporting an arm of a user, comprising: a harness configured to be worn on a body of a user, the harness comprising a shoulder harness configured to be worn over or around one or both shoulders of the user and a bracket comprising a first end fixed to the harness and a second end located above the shoulder of a user when the harness is worn by the user;
an arm support comprising an L-shaped first arm support bar pivotally coupled to the second end of the bracket such that the first arm support bar is rotatable horizontally about a vertical axis relative to the harness, and a single, unitary second arm support bar pivotally coupled to the first arm support bar such that the second arm support bar is rotatable about a second axis generally orthogonal to the vertical axis to accommodate movement of the arm while following the movement without substantially interfering with the movement of the user's arm, the second arm support bar sized to terminate adjacent the user's upper arm such that the user's forearm remains unsupported; an arm rest carried by the second arm support bar such that the arm rest rotates about the second axis with the second arm support bar when the user raises and lowers the upper arm; and
a spring mechanism coupled to the first and second arm support bars, the spring mechanism being the exclusive energy source applying an offsetting force to the second arm support bar to at least partially offset a gravitational force acting on the arm as the user moves and the arm support follows the movement of the user's arm.

11. The system of claim 10, wherein the first arm support bar is pivotally coupled to the second end of the bracket at a first pivot point that is translationally fixed at a location above or behind a shoulder of the user when the harness is worn by the user.

12. The system of claim 10, wherein the spring mechanism is configured to apply a variable offsetting force acting on the arm support.

13. A system for supporting an arm of a user, comprising:
a harness configured to be worn on a body of a user, the harness comprising an attachment band configured to be worn around the torso of the user, a shoulder harness configured to be worn over or around one or both shoulders of the user, and one or more support members extending between the attachment band and the shoulder harness;
a bracket comprising a first end mounted to the harness and a second end substantially fixedly located above the shoulder of a user when the harness is worn by the user; and
an arm support comprising:
a L-shaped first arm support segment comprising a first end pivotally coupled to the second end of the bracket such that a second end of the first arm support segment is positioned adjacent an upper arm of the user adjacent the shoulder and is rotatable substantially horizontally about a first axis relative to the harness;
a single, unitary second arm support bar comprising a first end pivotally coupled to the second end of the first arm support segment such that a second free end of the second arm support bar is rotatable substantially vertically about a second axis substantially orthogonal to the first axis to accommodate movement of the arm while following the movement without substantially interfering with the movement of the user's arm, wherein the second arm support bar is sized to extend along the user's upper arm and terminate above the user's elbow for supporting the user's upper arm while the user's forearm remains unsupported;
an arm rest mounted on the second end of the second arm support bar such that the arm rest rotates about the second axis with the second arm support bar to support the user's upper arm when the user raises and lowers the upper arm; and a spring compensation element coupled to the second arm support bar consisting essentially of a spring mechanism configured to apply an offsetting force to the arm bracket to at least partially offset a gravitational force acting on the arm as the user moves and the arm support follows the movement of the user's arm.

14. The system of claim 13, wherein the spring compensation element comprises a spring member coupled to the first and second arm support segments.

\* \* \* \* \*